US009513286B2

(12) United States Patent
Loughran, Jr. et al.

(10) Patent No.: US 9,513,286 B2
(45) Date of Patent: Dec. 6, 2016

(54) DIFFERENTIALLY EXPRESSED GENES IN LARGE GRANULAR LYMPHOCYTE LEUKEMIA

(75) Inventors: Thomas P. Loughran, Jr., Hummelstown, PA (US); Ravi Kothapalli, Wesley Chapel, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 1576 days.

(21) Appl. No.: 11/476,407

(22) Filed: Jun. 28, 2006

(65) Prior Publication Data
US 2007/0020666 A1 Jan. 25, 2007

Related U.S. Application Data

(63) Continuation of application No. 10/766,157, filed on Jan. 28, 2004, now abandoned.

(60) Provisional application No. 60/319,910, filed on Jan. 28, 2003.

(51) Int. Cl.
*G01N 33/564* (2006.01)
*G01N 33/574* (2006.01)
*C12Q 1/68* (2006.01)

(52) U.S. Cl.
CPC .......... *G01N 33/564* (2013.01); *C12Q 1/6883* (2013.01); *C12Q 1/6886* (2013.01); *G01N 33/57426* (2013.01); *C12Q 1/6837* (2013.01); *C12Q 2600/136* (2013.01); *C12Q 2600/158* (2013.01); *G01N 2500/00* (2013.01)

(58) Field of Classification Search
None
See application file for complete search history.

(56) References Cited

U.S. PATENT DOCUMENTS

| 7,220,580 B2 * | 5/2007 | Loughran et al. ............ 435/325 |
| 2001/0044104 A1 | 11/2001 | Warrington et al. |
| 2002/0035243 A1 | 3/2002 | Imfeld et al. |
| 2002/0120100 A1 | 8/2002 | Bonny |
| 2003/0032594 A1 | 2/2003 | Bonny |
| 2003/0190654 A1 | 10/2003 | Heidenreich et al. |
| 2004/0072237 A1 * | 4/2004 | Schweitzer .................. 435/7.1 |

FOREIGN PATENT DOCUMENTS

| WO | WO 99/09206 A1 | 2/1999 |
| WO | WO 01/36646 A1 | 5/2001 |
| WO | WO 02/057311 A2 | 7/2002 |

OTHER PUBLICATIONS

Grossman et al, Blood, vol. 90, p. 783-794, 1997.*
Kothaplalli et al, Blood vol. 98, No. 22, part 1, 302a, 2001, abstract.*
Makishima et al, British J Haematology, vol. 118 p. 462-469, Aug. 2002, IDS of Jun. 28, 2006, R9.*
Kothaplalli et al, Biochim Biophys Acta vol. 1579, p. 117-123, Dec. 12, 2002, IDS of Jun. 28, 2006, R21.*
Kothaplalli et al. BMC Bioinformatics, 3: 22, Aug. 23, 2002.*
Kothapalli et al, Blood, vol. 98, No. 11, part 1 PP302a, abstract, published Nov. 2001.*
Kothapalli et al, Experimental hematology 28:115, 2000, abstract.*
Shvidel et al Hematol J 3:32-7, 2002, abstrac.*
Lacy et al, Blood, 87: 3000-3008, 1996.*
Callan, M. et al. "CD8+T-cell selection, function, and death in the primary Immune response in vivo" *The Journal of Clinical investigation*, Nov. 2000, pp. 1251-1261, vol. 106, No. 10.
Loughran, T. P. Jr, "Clonal Diseases of Large Granular Lymphocytes" *Blood*, Jul. 1, 1993, pp. 1-14. vol. 82, No. 1.
Oshimi, K. et al. "Perforin Gene Expression in Granular Lymphocyte Proliferative Disorders" *Blood*, Feb. 1, 1990, pp, 704-708, vol. 75, No. 3.
Loughran, T. P. Jr. et al. "Anti-CD3 Monoclonal Antibody-Medicated Cytotoxicity Occurs Through an Interleukin-2-Independent Pathway in CD3+ Large Granular Lymphocytes" *Blood*, Feb. 15, 1990, pp. 935-940, vol. 75, No. 4.
Lamy, T. et al. "Dysregulation of CD95/CD95 Ligand-Apoptotic Pathway in CD3+Large Granular Lymphocyte Leukemia" *Blood*, Dec. 15, 1998, pp, 4771-4777, vol. 92, No. 12.
Kasten-Sportes, C. et al. "T-Cell Receptor Gene Rearrangement in T-Cell Large Granular Leukocyte Leukemia: Preferential V α but Diverse J α Usage in One of Five Patients" *Blood*, Feb. 1, 1994, pp. 767-775, vol. 83. No. 3.
Hoshino, S. et al. "Activation via the CD3 and CD16 Pathway Mediates Interleukin-2-Dependent Autocrine Proliferation of Granular Lymphocytes in Patients With Granular Lymphocyte Proliferative Disorders" *Blood*, Dec. 15, 1991, pp. 3232-3240, vol. 78, No. 12.
Daibata, M. et al. "Differential Gene-Expression Profiling in the Leukemia Cell Lines Derived From Indolent and Aggressive Phases of CD56* T-Cell Large Granular Lymphocyte Leukemia" *Int. J. Cancer*, 2004, pp, 845-851, vol. 108.

(Continued)

*Primary Examiner* — Lei Yao
(74) *Attorney, Agent, or Firm* — Saliwanchik, Lloyd & Eisenschenk

(57) ABSTRACT

The subject invention concerns gene sequences and the use thereof as markers for large granular lymphocyte (LGL) leukemia. The gene sequences of the invention are differentially expressed in LGL. Another aspect of the invention pertains to therapeutic compositions directed to gene expression and gene products of differentially expressed genes in LGL. The invention also concerns methods for screening and identifying compositions that may be of therapeutic benefit to patients having LGL leukemia and/or autoimmune disorders. In addition, because a large fraction of patients with T-LGL leukemia also have rheumatoid arthritis, these differentially expressed genes also represent novel targets for the diagnosis, prevention or treatment of rheumatoid arthritis and other autoimmune diseases.

12 Claims, 13 Drawing Sheets

(56) References Cited

OTHER PUBLICATIONS

Makishima, H. et al. "DNA microarray analysis of T cell-type lymphoproliferative disease of granular lymphocytes" *British Journal of Haematology*, 2002, pp. 462-469, vol. 118.

Kothapalli, R. et al. "Constitutive expression of cytotoxic proteases and down-regulation of protease inhibitors in LGL leukemia" *International Journal of Oncology*, Jan. 1, 2003, pp. 33-39, vol. 22, No. 1.

Perzova, R. et al. "Constitutive expression of Fas ligand in large granular lymphocyte leukaemia" *British Journal of Haematology*, 1997, pp. 123-126, vol. 97.

Weston, G. S. et al. "Granzymes as Potential Targets for Rational Drug Design" *Current Medicinal Chemistry*, 1996, pp. 37-46, vol. 3.

Epstein, C. B. et al. "Microarray technology-enhanced versatility, persistent challenge" *Current Opinion in Biotechnology*, Feb. 1, 2000, pp. 36-41, vol. 11, No. 1.

McManus, M. T. et al. "Gene Silencing in Mammals by Small Interfering RNAs" *Nature Reviews Genetics*, Oct. 2002, pp. 737-747, vol. 3.

Takashita, E. et al. "Destruction of hematapoietic microenvironment by cytotoxic T cells" *Experimental Hematology*, 1997, pp. 1034-1041, vol. 25, No. 10.

Crabtree, G. R. et al. "Signal transmission between the plasma membrane and nucleus of T lymphocytes" *Ann Rev Biochem*, 1994, pp. 1045-1063, vol. 63.

Butz, E. A. et al. "Massive expansion of antigen-specific CD8+ T cells during an acute virus infection" *Immunity*, 1998, pp. 167-175, vol. 8.

Engler-Blum, G. et al. "Reduction of background in problems in non-radioactive Northern blot analysis enables higher sensitivity than $^{32}$P-based hybridizations" *Anal. Biochem*, 1993, pp. 235-244, vol. 210.

Grakoui, A. et al. "The immunological synapse: a molecular machine controlling T-cell activation" *Scicence*, 1999, pp. 221-227, vol. 285.

Kothapalli, R. et al. "Microarray results: how accurate are they?" *BMC Bioinformatics*, 2002, pp. 1-10, vol, 3.

Kothapalli, R. et al. "Characterization of a human sphingosine-1-phosphate receptor gene ($SIP_5$) and it differential expression in LGL leukemia" *Biochimica et Biophysics Acta*, 2002, pp. 117-123, vol. 1579.

Kothapalli, R. et al. "Characterization of a variant of PAC-1 in large granular lymphocyte leukemia" *Protein Expression & Purification*, 2003, pp. 52-60, vol. 32.

Lamy, T. et al. "Current concepts: large granular lymphocyte leukemia" *Blood Rev.*, 1999, pp. 2311-244, vol. 13.

Nagata, S. et al. "The Fas death factor" *Science*, 1995, pp. 1449-1456, vol. 267.

Zambello, R. et al. "Analysis of the T Cell Receptor in the Lymphoproliferative Disease of Granular Lymphocytes: Superantigen Activation of Clonal CD3+ Granular Lymphocytes" *Cancer Res.*, 1995, pp. 6140-6145, vol. 55.

Zimmermann, C. et al. "Homeostatic regulation of $CD8^+$T Cells after antigen challenge in the absence of Fas (CD95)"*Eur. J. Immunot*, 1996, pp. 2903-2910, vol. 26.

Koo, G. C. et al. "Association of Serine Protease with the Rise of Intracellular Calcium in Cytotoxic T Lymphocytes" *Cellular Immunology*, 1996, pp. 107-115, vol. 174, Article No. 0300.

Smyth, M. J. et al. "Distinct Granzyme Expression in Human $CD3^-CD56^+$Large Granular- and $CD3^-CD56^+$Small High Density-Lymphocytes Displaying Non-MHC-Restricted Cytolytic Activity" *Journal of Leukocyte Biology*, Jan. 1995, pp. 88-93, vol. 57, No. 1.

Robertson, M. J. et al. "Characterization of a Cell Line, NKL, Derived from an Aggressive Human Natural Killer Cell Leukemia" *Experimental Hematology*, 1996, pp. 406-415, vol. 24, No. 3.

\* cited by examiner

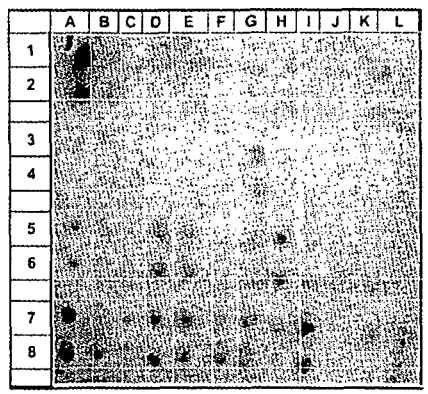
FIG. 5A
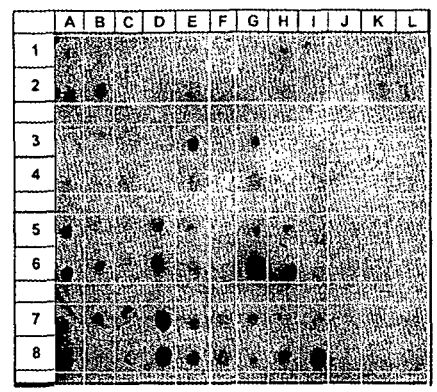
FIG. 5B
|   | A | B | C | D | E | F | G | H | I | J | K | L |
|---|---|---|---|---|---|---|---|---|---|---|---|---|
| 1 2 | Pos | Pos | Neg | Neg | ENA-78 | GCSF | GM-CSF | GRO | GRO-α | I-309 | IL-1α | IL-1β |
| 3 4 | IL-2 | IL-3 | IL-4 | IL-5 | IL-6 | IL-7 | IL-8 | IL-10 | IL-12 | IL-13 | IL-15 | IFN-γ |
| 5 6 | MCP-1 | MCP-2 | MCP-3 | MCSF | MDC | MIG | MIP-1β | MIP-1α | RANTES | SCF | SDF-1 | TARC |
| 7 8 | TGF-β | TNF-α | TNF-β | EGF | IGF-1 | Ang | OSM | Tpo | VEGF | PDGF-β | Leptin | Pos |
FIG. 5C

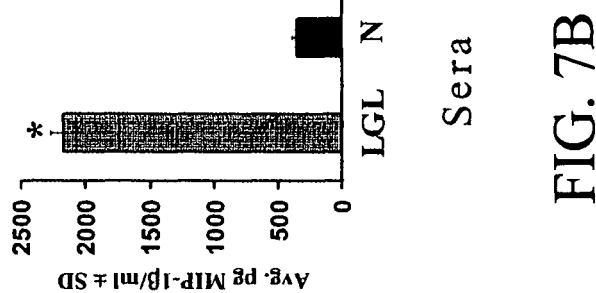
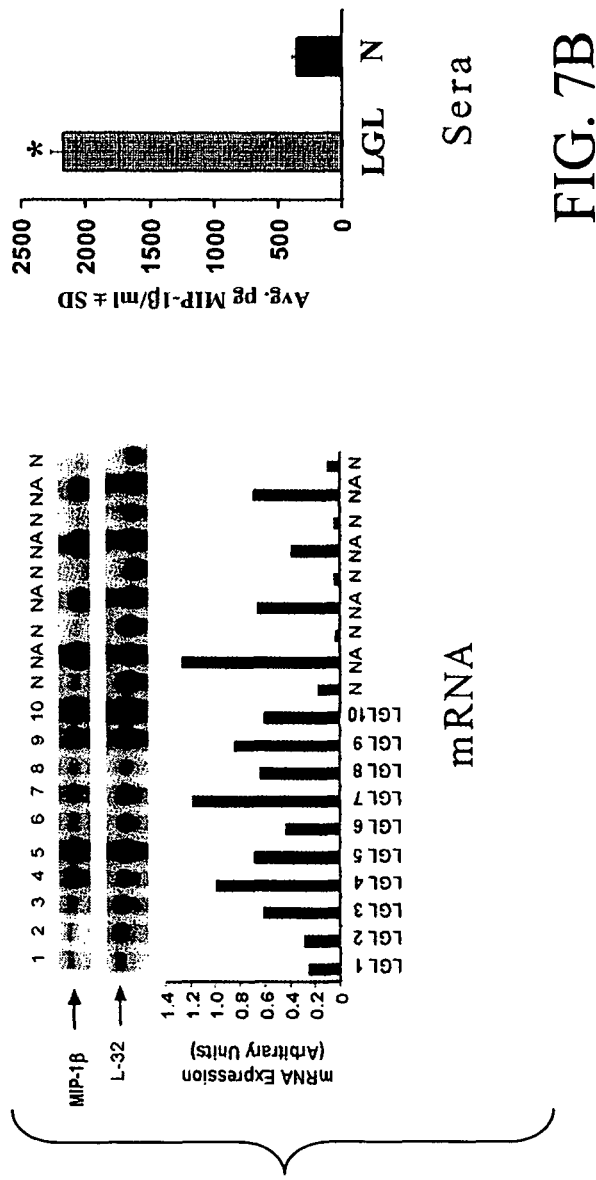
FIG. 7B
FIG. 7A

DIFFERENTIALLY EXPRESSED GENES IN LARGE GRANULAR LYMPHOCYTE LEUKEMIA

CROSS-REFERENCE TO RELATED APPLICATION

This application is a continuation of co-pending application U.S. Ser. No. 10/766,157, filed Jan. 28, 2004, now abandoned, which claims the benefit of U.S. Provisional Application Ser. No. 60/319,910, filed Jan. 28, 2003, which is hereby incorporated by reference herein in its entirety.

This invention was made with government support under the Veterans Administration, grant number CA83947, and the National Cancer Institute, grant number CA90633. The government has certain rights in the invention.

BACKGROUND OF THE INVENTION

Large granular lymphocyte (LGL) leukemia is a human lymphoproliferative disorder often associated with autoimmune disease, such as rheumatoid arthritis. The etiology of LGL leukemia is not known. Large granular lymphocyte are a morphologically recognizable lymphoid subset comprising 10%-15% of peripheral blood mononuclear cells. LGL can be divided into two major lineages: CD3-negative cells (CD3−) and CD3-positive cells (CD3+). CD3−LGL are natural killer (NK) cells that mediate non-major histocompatibility complex (MHC)-restricted cytotoxicity and do not express the CD3/T-cell receptor (TCR) complex or rearrange TCR genes. CD3+LGL are T-cells that do express CD3/TCR complex and rearrange TCR genes. A syndrome of increased numbers of circulating LGL associated with chronic neutropenia was first recognized as a distinct clinical entity in 1977. LGL proliferations are now known to be clonally derived from either of their counterparts (CD3− or CD3+LGL). Although the etiology of LGL leukemia has not been fully elucidated, some evidence suggests that the initiation event may involve an HTLV-I like retrovirus.

Examination of the peripheral blood is critical for establishing the diagnosis of LGL leukemia. Characteristic features of the disease include larger than normal lymphocytes with abundant pale cytoplasm and prominent azurophilic granules. Patients with clonal CD3+LGL (T-LGL) possess clonally derived lymphocytes with a CD3+, CD16+ and CD57+ phenotype. Autoimmune features are characteristic of this disease, and these patients resemble that of Felty's syndrome and present with the clinical triad of rheumatoid arthritis, neutropenia and splenomegaly. Morbidity and mortality most often results from infections acquired during severe neutropenia. The mechanism underlying the neutropenia is not well understood. Interestingly up to 40% of patients with T-cell LGL have rheumatoid arthritis. Although the cause of T-LGL leukemia and the events initiating the development of rheumatoid arthritis are now known, it has been hypothesized that there may be a common etiology underlying both diseases. Patients with NK-LGL possess clonally expanded LGL with a CD3−, CD4−, CD8−, CD16+ and CD56+ phenotype. In spite of aggressive treatment with multi-agent chemotherapy, 80% of these patients die within two months of diagnosis due to disseminated disease with multi-organ failure.

Cytotoxic T lymphocytes (CTL) are $CD8^+$ T cells activated in response to antigen. Such CTL can be categorized into naïve $CD8^+$ cells, terminally differentiated effector cells which are likely to undergo apoptosis, and a minor proportion of long-term $CD8^+$ memory cells. These memory cells proliferate in the presence of antigen (Butz et al., 1998). Cell-mediated killing by cytotoxic T-lymphocytes is an important event to protect the host against viral infection and tumor cell proliferation (Crabtree et al., 1994; Grakoui et al., 1999). Cytotoxic T cells are loaded with granules containing various effector molecules that are capable of killing target cells. Upon contact with target cells, the cytotoxic cells release cytotoxic molecules vectorially into the target cells and destroy them. Once the antigen is cleared from the system, the majority of the cytotoxic T cells (terminally differentiated cells) die primarily through Fas-mediated apoptosis in order to maintain homeostasis (Nagata et al., 1995; Callan et al., 2000; Zimmerman et al., 1996). In lymphoproliferative disorders such homeostasis is not maintained, resulting in the accumulation of a large number of lymphocytes. This may be due to defective apoptotic pathways in effector $CD8^+$ cells or due to the constant presence of antigen leading to a continuous proliferation of cells.

The T cell form of large granular lymphocyte (LGL) leukemia is a lymphoproliferative disorder often associated with autoimmune disease (Loughran, Jr., 1993; Lamy et al., 1999). Several lines of research suggest that leukemic LGL are antigen activated CTL. Leukemic LGL display an activated cytotoxic T-cell phenotype (Loughran, Jr., 1993). Activation of leukemic LGL can be triggered through CD3 and/or CD16 pathways (Hoshino et al., 1991; Loughran et al., 1990). Leukemic LGL constitutively express perforin and Fas ligand which, besides NK cells, are found expressed only in T cells activated for killing (Oshimi et al., 1990; Lamy et al., 1998). A restricted T cells receptor repertoire has been found in some studies of LGL leukemia, suggesting antigen selection (Zambello et al., 1995; Kasten-Sportes et al., 1994).

BRIEF SUMMARY OF THE INVENTION

The subject invention concerns materials and methods for screening, diagnosis, and treatment of LGL leukemia and autoimmune disorders. A series of both known and novel genes sequences that are differentially expressed in LGL leukemia has been identified. One aspect of the invention provides for the use of these genes as molecular markers for LGL leukemia and also as novel therapeutic targets for the disease. Thus, another aspect of the invention pertains to therapeutic compositions directed to gene expression and gene products of differentially expressed genes in LGL. The invention also concerns methods for screening and identifying compositions that may be of therapeutic benefit to patients having LGL leukemia and/or autoimmune disorders. In addition, because a large fraction of patients with T-LGL leukemia also have rheumatoid arthritis, these differentially expressed genes also represent novel targets for the diagnosis, prevention or treatment of rheumatoid arthritis and other autoimmune diseases.

BRIEF DESCRIPTION OF THE DRAWINGS

FIG. 1A shows a portion of the microarray showing the element F12 for granzyme B/H (indicated by the arrow, the cDNA fragment arrayed on microarray can hybridizes with both Granzyme B and H). FIG. 1B shows a portion of the microarray showing the element D4 for Cathepsin W (indicated by the arrow). FIG. 1C shows a portion of the microarray showing the element D2 for perforin (indicated by the arrow).

FIG. 2A is the Northern blot showing the expression of granzyme B/H. FIG. 2B is the Northern blot showing the expression of cathepsin W. FIG. 2C is the Northern blot analysis showing the expression of perforin. FIG. 2D is the Northern blot showing the expression of calpain.

FIG. 3A shows the hybridization profile for Granzyme B. FIG. 3B shows the hybridization profile for Granzyme H. A probe set, hAPO4, was obtained containing Granzyme B, H. These probes are very specific and distinguish between granzyme B and H. FIG. 3C shows the hybridization profile for Granzyme A. FIG. 3D shows the hybridization profile of Granzyme K. A probe set, hAPO4, was obtained containing Granzyme A, K. FIG. 3E shows the hybridization profile of perforin. FIG. 3F shows the hybridization profile of caspase-8. Probe sets, hAPO4 and hAPO3c, were obtained containing perforin and caspase-8.

FIGS. 5A-5C show protein array detection of cytokines from LGL leukemia and normal sera. Cytokine arrays were completed on 20 LGL leukemia and 6 normal sera pools as described in the Materials and Methods section. Depicted above is a membrane from a representative normal sera sample (FIG. 5A) and from LGL leukemia serum (FIG. 5B). Each sample was subjected to array and subsequent densitometry analyses minimum of two times. In this particular example, these densitometry analyses showed that ENA, GRO, IL-1α, IL-6, IL-8, MCP-2, MCP-3, MCSF, MIP-1β, MIP-1α, RANTES, EGF, ANG, OSM, and TRO were overexpressed in the LGL samples. FIG. 5C shows the layout of the cytokine antibodies deposited on the array. The names of the cytokines used in the array are: Epithelial cell-derived neutrophil attractant-78 (ENA)-78; granulocyte colony-stimulating factor (G-CSF); granulocyte monocyte-colony stimulating factor (GM-CSF); growth-regulated oncogene-alpha (GRO-α); interleukin—(IL-); interferon-gamma (INF-γ); monocyte chemoattractant protein—(MCP-); macrophage colony-stimulating factor (MCSF), macrophage-derived chemokine (MDC); monokine induced by interferon-gamma (MIG); macrophage inflammatory protein—(MIP-); regulated on activation, normal T expressed and secreted (RANTES); stem cell factor (SCF); stromal cell-derived factor-1 (SDF-1) alpha; thymus- and activation-regulated chemokine (TARC); transforming growth factor—(TGF-); tumor necrosis factor (TNF); epidermal growth factor (EGF), insulin-like growth factor I (IGF-I); angiotensin (Ang); oncostatin M (OSM); thrombopoietin (Tpo); vascular endothelial growth factor (VEGF); platelet-derived growth factor (PDGF); Positive (Pos); Negative (Neg).

FIG. 6B shows measurement of RANTES by ELISA. RANTES levels are displayed in ng/ml. Results represent the findings from two experiments. LGL: LGL leukemia sera, N: normal sera. *($p<0.001$): Determined by confidence interval testing and Z test to be significantly greater than normal levels.

FIGS. 7A and 7B show elevated MIP-1β expression in LGL leukemia. RPA data demonstrating the overexpression of MIP-1β is shown in FIG. 7A. RPAs were performed as described in the Materials and Methods section. LGL: leukemic LGL, N: normal cells, NA: activated normal cells. Bands corresponding to mRNA expression were quantified and normalized with the housekeeping gene, L32, using an ImageQuant program. Relative expression was given as arbitrary units for each sample. 10 leukemic samples and 5 normal samples were used for statistical analysis. T-tests were performed assuming unequal variances. The P value for MIP-1β was $p<0.001$. Serum MIP-1β levels were determined by ELISA as shown in FIG. 7B. MIP-1β levels are depicted in pg/ml. Results represent the findings from two experiments. LGL: LGL leukemia patients sera, N: normal sera. *($p<0.001$): determined by confidence interval testing and Z test to be significantly greater than normal levels.

FIG. 8A shows RPA for MIP-1α: 10 LGL leukemia samples and 5 normal samples were used for statistical analysis. T-tests were performed assuming unequal variances. The P value obtained for MIP-1α was $p<0.02$. FIG. 8B shows RPA for IL-1β: 12 LGL leukemia samples and 4 normal samples were tested for statistical analysis. T-test analyses were performed assuming unequal variances. The P value obtained for IL-1β was $p<0.05$. FIG. 8C shows RPA for IL-Ra: 12 LGL leukemia samples and 4 normal samples were processed for statistical analysis. T-tests were performed assuming unequal variances. The P value obtained for IL-1Ra mRNA was p<0.001.

FIG. 9A shows RPA for IL-10: 12 LGL leukemia samples and 4 normal samples were analyzed. T-tests were performed assuming unequal variances. The P value obtained for IL-10 was p<0.02. FIG. 9B shows RPA for IL-12p35: 12 LGL leukemia samples and 4 normal samples were analyzed. T-tests were performed assuming unequal variances. The P value obtained for IL-12p35 was p<0.02. FIG. 9C shows RPA for IL-8: 10 LGL samples and 5 normal samples were used for statistical analysis. T-tests were performed assuming unequal variances. The P value obtained for IL-8 was p<0.055.

FIG. 10A shows RPA for IFNγ: 12 LGL leukemia samples and 4 normal samples were analyzed. T-tests were performed assuming unequal variances. The P value obtained for IFNγ was p<0.02. FIG. 10B shows RPA for IL-18: 10 LGL leukemia samples and 5 normal samples were analyzed. The P value obtained for IL-18 was p<0.01.

DETAILED DISCLOSURE OF THE INVENTION

Figure 1A:
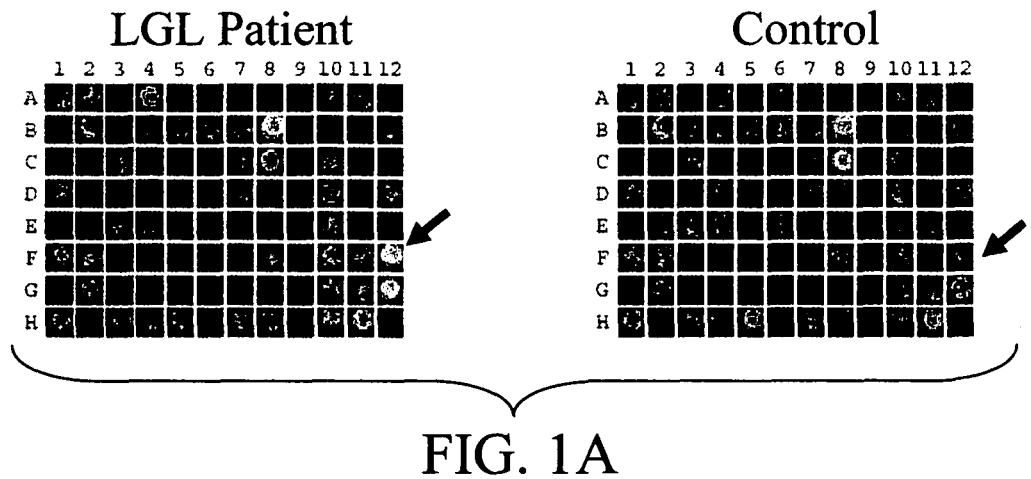
FIGS. 1A-1C show the cDNA microarray portions showing the expression of granzyme B/H, cathepsin W (Lymphopain) and perforin. cDNA microarray (UniGEM-V from Incyte Genomics) hybridized with the fluorescent probes prepared from mRNA isolated from PBMC of LGL leukemic patients (red) and from mRNA isolated from normal control (green). Images show the hybridization profile for an LGL patient and for the normal control. A color bar at the bottom shows the increased pattern of gene expression from left to right.

The subject invention concerns methods and materials for screening for, detecting, and diagnosing LGL leukemia and autoimmune disorders in a person or animal. Using a combination of microarray, Rnase protection assay and Northern Blot analysis, a series of both known and novel genes that are differentially expressed in LGL were identified. A list of genes that are differentially expressed in LGL leukemia are shown in Tables 1, 2, and 3. Table 1 identifies differentially expressed genes in LGL1 and LGL2. This data is based on Incyte Genomics and Affymetrix Chip FL 6800. Table 2 identifies genes that are upregulated in LGL1, LGL2, and LGL3/RA. This data is based on Affymetrix U 95. Table 3 identifies genes that are downregulated in LGL leukemia patients when compared to normal. This data is based on Affymetrix U 95. These genes can be used as biological markers for LGL leukemia. Differentially expressed genes identified in the present invention can also be used as therapeutic targets for the treatment or prevention of LGL leukemia and also rheumatoid arthritis and other autoimmune diseases. Several cytokines that are constitutively produced in LGL were also identified using Rnase protection assays, cytokine protein array screening, and ELISAs.

One embodiment of a method of the invention comprises obtaining a biological sample from a person or animal, and screening for upregulated expression of a gene or genes whose expression is upregulated in LGL and/or screening for downregulated expression of a gene or genes whose expression is downregulated in LGL. Quantitative or qualitative expression can be determined using any suitable method known in the art including, but not limited to, reverse transcription-polymerase chain reaction (RT-PCR), cDNA or oligonucleotide microarray analysis, and Northern blot analysis. Methods for polymerase chain reaction (PCR) are known in the art and have been described in U.S. Pat. Nos. 4,683,195; 4,683,202; and 4,800,159.

In one embodiment of the methods, RNA from a patient's cells is screened for changes in RNA expression of targeted genes as compared to the levels of expression observed for RNA expression of the same genes from a normal or non-LGL patient or compared to a control RNA. In one embodiment, genes encoding proteases, cytokines, and/or other molecules identified herein as differentially expressed in LGL are screened for upregulation of expression, which is indicative of LGL leukemia and/or an autoimmune disorder. In another embodiment, genes encoding protease inhibitors and/or other molecules are screened for downregulation, which is indicative of LGL leukemia and/or an autoimmune disorder. In a further embodiment, genes encoding proteases, cytokines, and/or other molecules are screened for upregulation of expression and genes encoding protease inhibitors and/or other molecules are screened for downregulation of expression. Genes whose expression is upregulated in LGL and which are contemplated within the scope of the invention include, but are not limited to, protease encoding genes, for example, serine proteases (granzymes A, B, H, and K), cysteine proteases (cathepsin C and W), calpain small subunit and caspase-8, and cytokine encoding genes, for example, RANTES, MIP-1alpha, MIP-1beta, IL-1 beta, IL-8, IL-1Ra, IFN-gamma, IL-18, IL-10, and IL-12 p35. Genes whose expression is downregulated in LGL and which are contemplated within the scope of the invention include, but are not limited to, protease inhibitor encoding genes, for example, cystatin C and A, α-1 antitrypsin, and metalloproteinase inhibitors. Any embodiment of the invention can also optionally include screening for upregulation of genes encoding perforins, A 20, phosphatase in activated cells (PAC-1) (Kothapalli et al., 2003), NGK2 receptors, sphingosine-1-phosphate receptor (Kothapalli et al., 2002b), and other genes whose expression is upregulated in LGL as shown in Tables 1 and 2. Any embodiment of the invention can also optionally include screening for downregulation of other genes whose expression is downregulated in LGL as shown in Tables 1 and 3.

In a further embodiment of the subject methods, a biological sample from a person or animal is obtained, and screened for expression of, or increased level of expression of, a protein that is encoded by a gene whose expression is upregulated in LGL and/or screening for lack of expression, or decreased level of expression of, a protein that is encoded by a gene whose expression is downregulated in LGL. Quantitative or qualitative expression can be determined using any suitable method known in the art including, but not limited to ELISA assay, Western blot analysis, and protein array screening.

In one embodiment of the methods, protein from a patient's cells is screened for changes in levels of expression of protein of a targeted gene as compared to the levels of expression observed for protein of the same gene from a normal or non-LGL patient or compared to a control protein level. In one embodiment, proteases, cytokines, and/or other molecules identified herein as differentially expressed in LGL are screened for increased level of expression, which is indicative of LGL leukemia and/or an autoimmune disorder. In another embodiment, protease inhibitors and/or other molecules are screened for decreased level of expression, which is indicative of LGL leukemia and/or an autoimmune disorder. In a further embodiment, proteases, cytokines and/or other molecules are screened for increased level of expression and protease inhibitors and/or other molecules are screened for decreased level of expression. Proteins whose expression is increased in LGL and are contemplated within the scope of the invention include protease encoding genes, for example, serine proteases (granzymes A, B, H, and K), cysteine proteases (cathepsin C and W), calpain small subunit and caspase-8, and cytokine encoding genes, for example, RANTES, MIP-1alpha, MIP-1beta, IL-1 beta, IL-8, IL-1Ra, IFN-gamma, IL-18, IL-10, and IL-12 p35. Proteins whose expression is decreased in LGL and are contemplated within the scope of the invention include protease inhibitor encoding genes, for example, cystatin C and A, α-1 antitrypsin, and metalloproteinase inhibitors. Any embodiment of the invention can also optionally include screening for increased expression of perforins, A 20, phosphatase in activated cells (PAC-1), NGK2 receptors, and other proteins whose expression is increased in LGL as shown in Tables 1 and 2. Any embodiment of the invention can also optionally include screening for decreased expression of other proteins whose expression is decreased in LGL as shown in Tables 1 and 3.

One can compare expression results from a method of the present invention with a statistically significant expression value obtained from a reference group of normal patients and/or patients that have LGL leukemia in order to determine whether the test sample exhibits increased or decreased or unchanged levels of expression of a gene or gene product of the invention.

In one embodiment of the subject methods, the expression of at least five genes or gene products whose upregulation is associated with LGL is determined. In another embodiment, the expression of at least ten genes or gene products whose upregulation is associated with LGL is determined. In a further embodiment, the expression of at least 15 genes or gene products whose upregulation is associated with LGL is determined. In still a further embodiment, the expression of at least 20, at least 25, at least 30, at least 35, or at least 40 or more genes or gene products whose upregulation is associated with LGL is determined.

In one embodiment of the subject methods, the expression of at least five genes or gene products whose downregulation is associated with LGL is determined. In another embodiment, the expression of at least ten genes or gene products whose downregulation is associated with LGL is determined. In a further embodiment, the expression of at least 15 genes or gene products whose downregulation is associated with LGL is determined. In still a further embodiment, the expression of at least 20, at least 25, at least 30, at least 35, or at least 40 or more genes or gene products whose downregulation is associated with LGL is determined.

The biological sample used in the methods and materials of the invention can be from any suitable biological tissue or fluid, including but not limited to bone marrow, lymph node, spleen, peripheral blood, lymph fluid, serous fluid, urine, saliva, and the like.

The subject invention also concerns kits comprising materials and compositions for use in screening for, detecting and diagnosing LGL or autoimmune disorders. The materials provide for detecting or determining expression of genes, and/or proteins encoded thereby, whose expression is differentially upregulated or downregulated in LGL as compared to expression levels in normal cells. In one embodiment, the screening materials comprise an array having one or more target gene or polynucleotide sequence whose expression is upregulated or downregulated in LGL. Nucleic acid samples can be obtained from a person or animal and the level of expression in the person or animal of the targeted gene or polynucleotide sequence provided on the array can be determined following hybridization of the sample with the array. In one embodiment, the array comprises one or more of the following target gene or polynucleotide sequences: granzymes A, B, H, and K; cathepsin C and W; calpain small subunit; caspase-8; cystatin C and A; α-1 antitrypsin; metalloproteinase inhibitor-8; perforins; A 20; PAC-1; NGK2 receptors; RANTES; MIP-1alpha; MIP-1beta; IL-1 beta; IL-8; IL-1Ra; IFN-gamma; IL-18; IL-10; IL-12 p35.

In another embodiment, a kit of the invention comprises oligonucleotide probes and PCR primers having sequences complementary to a sequence of a gene or polynucleotide (sequences of which correspond to the sequences in the accession numbers and identification numbers provided herein) whose expression is differentially expressed in LGL. In another embodiment, a kit of the invention provides for RT-PCR of nucleic acid samples for detecting expression levels of a gene or polynucleotide whose expression is differentially expressed in LGL.

In another embodiment, a kit of the invention comprises an antibody or antibodies that bind to gene products that are differentially expressed in LGL. The antibodies can be provided on an array.

The materials and compositions of a kit of the invention can be provided in one or more separate containers.

The subject invention concerns methods for treating LGL leukemia or an autoimmune disorder comprising administering an effective amount of a composition that inhibits the expression of a gene or polynucleotide, or that inhibits or blocks biological activity of a protein encoded by the gene or polynucleotide, that is upregulated in LGL. The subject invention also concerns methods for treating LGL leukemia or an autoimmune disorder comprising administering an effective amount of a composition that increases expression of a gene or polynucleotide, or that increases expression or level of a protein encoded by the gene or polynucleotide, that is downregulated in LGL.

Genes and polynucleotides whose expression is increased in LGL and can be the targets for inhibition in the subject methods include, but are not limited to, protease encoding genes, for example, serine proteases (granzymes A, B, H, and K), cysteine proteases (cathepsin C and W), calpain small subunit and caspase-8, and cytokine encoding genes, for example, RANTES, MIP-1alpha, MIP-1beta, IL-1 beta, IL-8, IL-1Ra, IFN-gamma, IL-18, IL-10, and IL-12 p35. Genes and polynucleotides whose expression is decreased in LGL and can be the targets for increased expression include, but are not limited to, protease inhibitor encoding genes, for example, cystatin C and A, α-1 antitrypsin, and metalloproteinase inhibitors. Any embodiment of the methods of the invention can also optionally include inhibiting expression of genes or polynucleotides that encode perforins, A 20, phosphatase in activated cells (PAC-1), NGK2 receptors, and other proteins whose expression is increased in LGL as shown in Tables 1 and 2, and/or increasing expression of other genes or polynucleotides whose expression is decreased in LGL as shown in Tables 1 and 3. One embodiment of the subject method comprises upregulating or increasing expression of genes encoding protease inhibitors or contacting an LGL with a protease inhibitor whose expression is downregulated in LGL.

Means for inhibiting expression of a specific targeted gene are known in the art and include antisense nucleic acid inhibition and RNA interference (RNAi). Means for inhibiting or blocking biological activity of a protein are also known in the art and include, for example, antibodies that specifically bind to a protein and block biological activity of the protein or that bind to the cellular receptor for the protein and prevent or inhibit binding of the protein to the receptor. Peptides can also be used that bind to a protein or receptor and block biological activity.

Polynucleotides that provide for transcribed sequences that are at least partially complementary to the transcribed sequence of a gene whose expression is upregulated in LGL, such as a gene encoding a protease enzyme or a cytokine, are also contemplated within the scope of the present invention. Such polynucleotides are referred to herein as antisense polynucleotides and the sequences are antisense sequences. Transcription of the antisense sequence results in production of RNA which is at least partially complementary to RNA transcribed from a gene. In one embodiment, the polynucleotide comprises a nucleotide sequence that is antisense to a sequence of a gene having a nucleotide sequence disclosed in an accession number or identification number herein. The polynucleotide does not have to be identical in sequence to or the same length as the endogenous gene sequence. The polynucleotide used for antisense inhibition can be shorter in length than the full-length gene sequence. For example, a polynucleotide can be used that corresponds to the 5'-end or the 3'-end of the endogenous gene.

The polynucleotide sequence that is complementary to a sequence of an mRNA of a target gene whose expression is to be inhibited is selected to be of sufficient length to bind to the mRNA and inhibit expression of the enzyme. The sequence is preferably between 10 and 5000 nucleotides in length. More preferably, the sequence is between 20 and 2000 nucleotides in length. Most preferably, the sequence is between 50 and 1000 nucleotides in length. The sequence transcribed from the antisense polynucleotide may be complementary to any sequence of the RNA transcribed from the target gene, including the 5' non-coding sequence, 3' non-coding sequence, introns, the coding sequence, or any portion thereof.

RNA interference (RNAi) can also be used to suppress or inhibit expression of an endogenous gene (McManus and Sharp, 2002; published U.S. patent application No. US2003/0190654 A1; published international application No. PCT/GB00/04404). In one embodiment of RNAi, short interfering double-stranded RNAs (siRNA) of about 20-25 nucleotides, and more typically of 21-23 nucleotides, in size and complementary to strands of the gene to be silenced are provided in a cell. For example, siRNAs that have 20-25 nucleotide, or 21-23 nucleotide, strands complementary to a nucleotide sequence of a gene whose expression that is upregulated in LGL are contemplated within the scope of the present invention. A vector that has a nucleotide sequence that when transcribed in a cell produces one or more separate siRNA strands that can then form the duplex form of the siRNA can be introduced into a targeted LGL cell.

In another embodiment of RNAi, a short hairpin RNA molecule (shRNA) is expressed in a cell. The shRNA, consisting of short inverted repeats separated by a small loop sequence, are expressed from a suitable vector. One inverted repeat is complementary to the gene target. The shRNA is then processed into an siRNA which suppresses expression of the gene to be silenced. A vector that has a nucleotide sequence that when transcribed in the cell produces one or more separate shRNA strands that can then form a hairpin can be introduced into a targeted LGL cell.

In addition to humans, animals can also be treated using the subject methods. Animals contemplated with the scope of the invention include, but are not limited to, mammals such as primates (monkey, chimpanzee, etc.), dog, cat, cow, pig, or horse, or other animals that have LGL leukemia or an autoimmune disorder.

The subject invention also concerns compositions for treating or preventing large granular lymphocyte (LGL) leukemia or an autoimmune disorder in a person or animal, wherein the composition comprises a means for inhibiting expression of a gene or polynucleotide, or inhibiting or blocking biological activity of a protein encoded by a gene or polynucleotide, whose expression is upregulated in LGL. In one embodiment, the composition comprises an antisense polynucleotide whose transcribed sequence is at least partially complementary to the transcribed sequence of a gene whose expression is upregulated in LGL, wherein expression of said gene is inhibited or blocked by expression of said antisense polynucleotide. In a further embodiment, the gene is granzymes A, B, H, or K; cathepsin C or W; calpain small subunit; caspase-8; perforins; A 20; PAC-1; NGK2 receptors; RANTES; MIP-1alpha; MIP-1beta; IL-1 beta; IL-8; IL-1Ra; IFN-gamma; IL-18; IL-10; or IL-12 p35, or one of the genes listed in Tables 1 and 2 whose expression is upregulated in LGL.

In another embodiment, a composition of the invention comprises an RNA that interferes with expression of a gene or polynucleotide whose expression is upregulated in LGL. In one embodiment, an RNA interfering molecule of the invention inhibits expression of one of the following genes: granzymes A, B, H, or K; cathepsin C or W; calpain small subunit; caspase-8; perforins; A 20; PAC-1; NGK2 receptors; RANTES; MIP-1alpha; MIP-1beta; IL-1 beta; IL-8; IL-1Ra; IFN-gamma; IL-18; IL-10; or IL-12 p35, or one of the genes listed in Tables 1 and 2 whose expression is upregulated in LGL. The RNA interfering molecule can be provided in the form of an siRNA.

In still another embodiment, a composition of the invention can comprise an antibody, or an antigen binding fragment thereof, that specifically binds to a protein encoded by a gene or polynucleotide whose expression is upregulated in LGL and blocks biological activity of the protein; an antibody, or an antigen binding fragment thereof, that specifically binds to a receptor for the protein and prevents or inhibits binding of the protein to the receptor; a peptide that binds to the protein or thereceptor and block biological activity of the protein or the receptor; or a combination of any of antibody or peptide.

The subject invention also concerns compositions for treating or preventing large granular lymphocyte (LGL) leukemia or an autoimmune disorder in a person or animal, wherein the composition comprises a means for increasing expression or levels of a protein encoded by a gene or polynucleotide whose expression is downregulated in LGL, such as the protease inhibitors cystatin C and A, α-1 antitrypsin, and metalloproteinase inhibitors.

In one embodiment, methods and compositions for treatment of LGL and/or autoimmune disorders can include inhibitors of those proteases whose expression is upregulated in LGL as described herein.

Therapeutic compositions of the invention can be delivered to a cell by direct contact with the cell or via a carrier means. Carrier means for delivering compositions to cells are known in the art and include encapsulating the composition in a liposome moiety, and attaching a oligonucleotide, peptide, etc. to a protein or nucleic acid that is targeted for delivery to the target cell. Published U.S. Patent Application Nos. 2003/0032594 and 2002/0120100 disclose amino acid sequences that can be coupled to another composition and that allows the composition to be translocated across biological membranes. Published U.S. Patent Application No. 2002/0035243 also describes compositions for transporting biological moieties across cell membranes for intracellular delivery.

For the treatment of oncological disorders, the therapeutic compositions of this invention can be administered to a patient in need of treatment in combination with other antitumor substances, with radiation therapy, and the like. These other substances or radiation treatments may be given at the same or different times as the therapeutic compositions of this invention. For example, therapeutic compositions of the present invention can be used in combination with mitotic inhibitors such as taxol or vinblastine, alkylating agents such as cyclophosphamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies.

Therapeutic application of the therapeutic compositions, and compositions containing them, can be accomplished by any suitable therapeutic method and technique presently or prospectively known to those skilled in the art. Therapeutic compositions can be administered by any suitable route known in the art including, for example, oral, nasal, rectal, and parenteral routes of administration. As used herein, the term parenteral includes subcutaneous, intravenous, intramuscular, and intrasternal administration, such as by injection. Administration of therapeutic compositions of the invention can be continuous or at distinct intervals as can be readily determined by a person skilled in the art.

Therapeutic compositions of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive composition is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with therapeutic compositions include ethanol, dimethyl sulfoxide, glycerol, alumina, starch, and equivalent carriers and diluents. To provide for the administration of such dosages for the desired therapeutic treatment, pharmaceutical compositions of the invention will advantageously comprise between about 0.1% and 99%, and especially, 1 and 15% by weight of the total of one or more of a therapeutic composition of the invention based on the weight of the total composition including carrier or diluent.

Therapeutic compositions of the subject invention can also be administered utilizing liposome technology, slow release capsules, implantable pumps, and biodegradable containers. These delivery methods can, advantageously, provide a uniform dosage over an extended period of time.

The subject invention also concerns a packaged dosage formulation comprising in one or more containers at least one therapeutic compound of the subject invention formulated in a pharmaceutically acceptable dosage.

The subject invention also concerns methods for screening for compounds useful in treating or preventing LGL leukemia. In one embodiment, an LGL cell is contacted with a test compound and nucleic acid isolated from the cell and screened for: 1) inhibition of those gene sequences that are upregulated in LGL, or 2) increased expression of those gene sequences that are downregulated in LGL, or 3) both screening for inhibition of those gene sequences that are upregulated in LGL and screening for increased expression of those gene sequences that are downregulated in LGL are performed. Those gene sequences that are typically upregulated in LGL and that can be used in the subject methods include, but are not limited to, genes encoding granzymes A, B, H, and K; cathepsin C and W; calpain small subunit; caspase-8; perforins; A 20; PAC-1; NGK2 receptors; RANTES; MIP-1alpha; MIP-1beta; IL-1 beta; IL-8; IL-1Ra; IFN-gamma; IL-18; IL-10; IL-12 p35. Those gene sequences that are typically downregulated in LGL and that can be used in the subject method include, but are not limited to, genes encoding cystatin C and A; α-1 antitrypsin; metalloproteinase inhibitors. Alternatively, one can screen the cells contacted with the test compound for increased or decreased production or levels of proteins encoded by genes or polynucleotides that are differentially expressed in LGL, such as granzymes A, B, H, and K; cathepsin C and W; calpain small subunit; caspase-8; perforins; A 20; PAC-1; NGK2 receptors; RANTES; MIP-1alpha; MIP-1beta; IL-1 beta; IL-8; IL-1Ra; IFN-gamma; IL-18; IL-10; IL-12 p35; cystatin C and A; α-1 antitrypsin; and metalloproteinase inhibitors. Compounds identified as inhibiting expression of upregulated sequences and/or increasing expression of downregulated sequences are potential candidates for use in treating LGL.

The subject invention also concerns methods for screening for compounds useful in treating or preventing autoimmune disorders associated with LGL. In one embodiment, a cell is contacted with a test compound and nucleic acid isolated from the cell and screened for: 1) inhibition of those gene sequences that are upregulated in LGL, or 2) increased expression of those gene sequences that are downregulated in LGL, or 3) both screening for inhibition of those gene sequences that are upregulated in LGL and screening for increased expression of those gene sequences that are downregulated in LGL are performed. Those gene sequences that are typically upregulated in LGL and that can be used in the subject methods include, but are not limited to, genes encoding granzymes A, B, H, and K; cathepsin C and W; calpain small subunit; caspase-8; perforins; A 20; PAC-1; NGK2 receptors; RANTES; MIP-1alpha; MIP-1beta; IL-1 beta; IL-8; IL-1Ra; IFN-gamma; IL-18; IL-10; IL-12 p35. Those gene sequences that are typically downregulated in LGL and that can be used in the subject method include, but are not limited to, genes encoding cystatin C and A; α-1 antitrypsin; metalloproteinase inhibitor. Compounds identified as inhibiting expression of upregulated sequences and/ or increasing expression of downregulated sequences are potential candidates for use in treating autoimmune disorders.

The subject invention also concerns variants of the genes and polynucleotides contemplated within the scope of the present invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Genes and polynucleotides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

Tm=81.5 C+16.6 Log [Na+]+0.41(% G+C)−0.61(% formamide)−600/length of duplex in base pairs.

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the sequences also fall within the scope of the subject invention. The polynucleotide sequence includes both the sense and antisense strands either as individual strands or in the duplex.

Nucleotide and amino acid sequences of genes, and proteins encoded thereby, that are contemplated within the scope of the present invention include those sequences provided in publicly accessible sequence databases such as Genbank and which are identified herein (such as in Tables 1, 2, and 3) by accession number or identification number, including those incorporated by reference.

All patents, patent applications, provisional applications, and publications referred to or cited herein are incorporated by reference in their entirety, including all sequences (including those identified by database accession number), figures and tables, to the extent they are not inconsistent with the explicit teachings of this specification.

Materials and Methods

Isolation of PBMC and RNA.

PBMC were isolated from whole blood using Ficoll-Hypaque density gradient centrifugation. These cells were suspended in Trizol reagent (GIBCO-BRL, Rockville, Md.) and total RNA was isolated immediately according to the manufacturer's instructions. Poly $A^+$ RNA was isolated from total RNA by using Oliogo-Tex mini mRNA kit (Qiagen, Valencia, Calif.) according to the manufacturer's recommendations. All patients selected had T cell form of LGL leukemia.

Activation of PBMC.

Normal PBMC were cultured in vitro and activated using PHA (Sigma Chemical Co., St. Louis, Mo.) (1 µg/ml, 2 days) and Interleukin-2 (IL-2) (100 U/ml, 10 days), then total RNA was isolated.

cDNA Microarray.

Microarray probing and analysis was done by Incyte Genomics. Briefly, one µg of Poly $(A)^+$ RNA isolated from PBMC of an LGL leukemia patient and a healthy individual was reverse transcribed to generate Cy3 and Cy5 fluorescent labeled cDNA probes. cDNA probes were competitively hybridized to a human UniGEM-V cDNA microarray containing 7075 immobilized cDNA fragments (4107 for known genes and 2968 ESTs). Microarrays were scanned in both Cy3 and Cy5 channels with Axon GenePix (Foster City) with a 10 µm resolution. Incyte GEMtools software (Incyte Pharmaceuticals, Inc., Palo Alto, Calif.) was used for image analysis. The elements were determined by gridding and region detection algorithm. The area surrounding each element image was used to calculate a local background and was subtracted from the total element signal. Background subtracted element signals were used to calculate the Cy3:Cy5 ratio. The average of the resulting total Cy3 and Cy5 signal provided a ratio that was used to balance or normalize the signals. P1 and P2 signals were the intensity reading obtained by the scanner for Cy3 and Cy5 channels. The balanced differential expression was calculated using the ratio between the P1 signal (intensity reading for probe 1) and the balanced P2 signal (intensity reading for probe 2 adjusted using the balanced coefficient).

Microarray Analysis Using Oligonucleotide Probe Arrays.

The HuGeneFL (contains 6800 genes) microarray chip obtained from Affymetrix (Santa Clara, Calif.) was used. Briefly total RNA isolated from normal PBMC of normal, normal sorted $CD8^+$ T cells and PBMC from two different LGL leukemia patients (designated herein as LGL 1 and LGL 2, respectively) were DNase treated and purified with a Qiagen kit. Approximately 10 µg of purified RNA was used to prepare double stranded cDNA (superscript GIBCO/BRL) using a T7 (dT)24 primer containing a T7 RNA polymerase promoter binding site. Biotinylated complementary RNA was prepared from 10 µg of cDNA and then fragmented to approximately 50 to 100 nucleotides. In vitro transcribed transcripts were hybridized to the HuGeneFL microarray chip for 16 h at 45° C. with constant rotation at 60 rpm. Chips were washed and stained by using Affymetrix fluidics station. Fluorescence intensity was measured for each chip and normalized to the fluorescence intensity for the entire chip.

Verification of the Clones.

GEM cDNA clones (each clone was supplied as a bacterial stab) were purchased from Incyte Genomics and streaked on to LB/agar plates containing the appropriate antibiotic. Individual colonies were picked and cultured in LB medium. Plasmid DNA was isolated and sequenced in order to verify the sequence identity.

Northern Blot Analysis.

Northern Blotting was done as described in the standard protocols (Sambrook, 1989). Briefly 10 µg of total RNA of each sample was denatured at 65° C. in RNA loading buffer, electrophoresed in a 1% agarose gel containing 2.2 M formaldehyde, then blotted onto a Nytran membrane (Schleicher & Schuell, Inc., Keene, N. H). The RNA was fixed to the membrane by UV cross-linking. cDNA probes were labeled with [$^{32}$P] and purified by Nick columns (Amersham Pharmacia Biotech AB, Piscataway, N.J.). Hybridization and washings of the blots were performed as described by Engler-Blum et al. (1993). The blots were exposed to X-ray films and after developing the film, the bands were quantitated by using the ImageQuant program and normalized with the housekeeping gene GAPDH.

RNase Protection Assay (RPA) for Proteases and Protease Inhibitors.

RPA was performed using the RNA isolated from leukemic LGL, normal PBMC and normal PBMC activated by IL-2 and PHA. Five µg of total RNA was hybridized to the in vitro transcribed hAPO4 and hAPO3c probe sets (PharMingen, SanDiego, Calif.), the RPA assay was performed according to the manufacture's protocol. After assay, the samples were resolved on a 5% polyacrylamide gel. The gel was dried and exposed to X-ray film. After developing the film, the bands were quantitated by using the ImageQuant program and normalized with the housekeeping gene, L32.

Western Immunoblotting.

Cells were lysed in a buffer containing 50 mM Tris-HCl (pH 7.6); 5 mM EDTA; 150 mM NaCl; 0.5% NP-40; 0.5% Triton X-100 containing 1 µg/ml leupeptin, aprotinin and antipain; 1 mM sodiumorthovanadate; and 0.5 mM PMSF (all reagents were obtained from Sigma Chemical Co. St. Louis, Mo.) 25 µg of total protein from each sample was subjected to 10% SDS-PAGE. Then the proteins were transferred to a membrane and Western blotting was performed by using the monoclonal antibody for granzyme B (2C5, Santa Cruz Biotechnology, Santa Cruz, Calif.) and the ECL technique as recommended by the manufacturer (Amersham Pharmacia Biotech, Piscataway, N.J.).

RNase Protection Assay (RPA) for Cytokines.

RPA was performed using RNA isolated from leukemic LGL, normal PBMCs and normal PBMCs activated by IL-2 and PHA. Five µg of total RNA was hybridized to in vitro transcribed cytokine multi-probe sets (RiboQuant, BD Biosciences, San Jose, Calif.) and the RPA assay was performed according to the manufacturer's protocol. The samples were resolved on a 5% polyacrylamide gel. The gel was dried and exposed to X-ray film. After developing the film, the bands were quantified by using the ImageQuant program (Molecular Dynamics, Sunnyvale, Calif.) and normalized against the housekeeping gene, L32.

Cytokine Protein Array Screening.

LGL leukemia sera were screened for relative cytokine levels by cytokine protein arrays, following the kit manufacturer's directions (RayBiotech, Inc., Norcross, Ga.). Twenty LGL leukemia sera and six sets of pooled normal sera (12 donors for test) were tested. Each protein array membrane contained a grid of capture antibodies specific for 43 different human cytokines. Briefly, membranes were blocked, and then incubated with 10 fold-diluted sera for 2 hours. After washing, the membrane-bound serum components were reacted with a biotin-conjugated anti-cytokine antibody cocktail. After the non-binding conjugates were removed, the membranes were incubated with HRP-conjugated strepavidin, and then washed a final time. HRP-biotin conjugated complexes indicating the presence of human cytokines was visualized by ECL reactions on film. A two-step process was used to determine relative expression. First, densitometry analysis was completed on individual membranes, which contained positive and negative controls. Then, the densitometry data for each LGL leukemia sample was compared to the corresponding data for normal sera and an expression ratio was derived. The significance of fold differences were determined by the use of confidence interval testing derived from the densitometry results of each experiment.

Cytokine ELISAs.

Cytokines were selected for quantification based on RPA and/or protein array results. In general, ELISAs were performed for all cytokines and chemokines with increased levels of mRNA expression, unless protein array blot identified no differential protein expression for a particular cytokine/chemokine. Interleukin-1β (IL-1β) and interleukin-8 (IL-8) were analyzed with OptEIA sets (PharMingen, San Diego, Calif.), interleukin-1 receptor antagonist (IL-1Ra) and IL-18, were analyzed with Quantikine kits (R&D Systems, Minneapolis, Minn.) and all others were analyzed with kits or antibody pairs from Pierce Endogen. Additional testing for serum IL-1β was completed using the R&D Systems IL-1β Quantikine kit. For ELISAs, 27 LGL leukemia sera, 13 normal sera representing the age and gender distribution of LGL leukemia (purchased from Florida Blood Services, St. Petersburg, Fla.) plus pooled sera from an additional 12 normal donors (Sigma) were tested. All analyses were performed twice with the exception of IL-1β analyses, which were performed in quadruplicate. Manufacturer's instructions were followed for each cytokine tested.

Following are examples which illustrate procedures for practicing the invention. These examples should not be construed as limiting. All percentages are by weight and all solvent mixture proportions are by volume unless otherwise noted.

EXAMPLE 1

Screening for Differential Expression of Genes in LGL

Figure 1B:
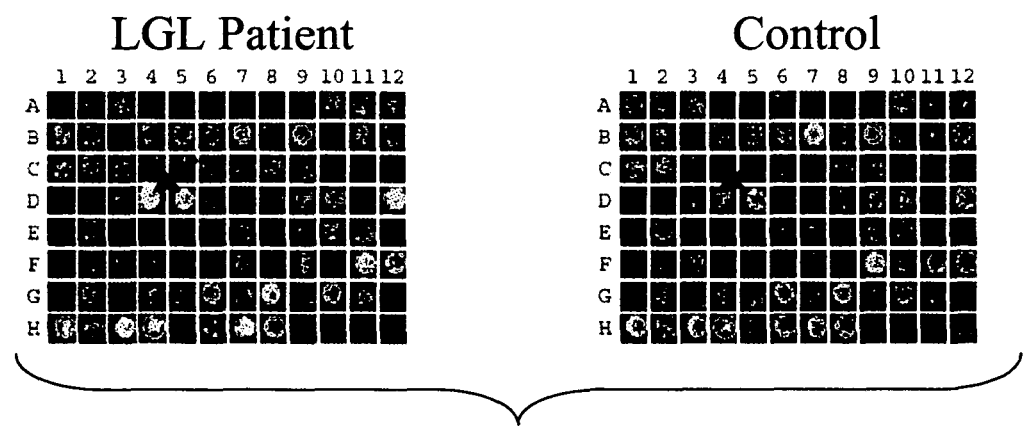
Figure 1C:
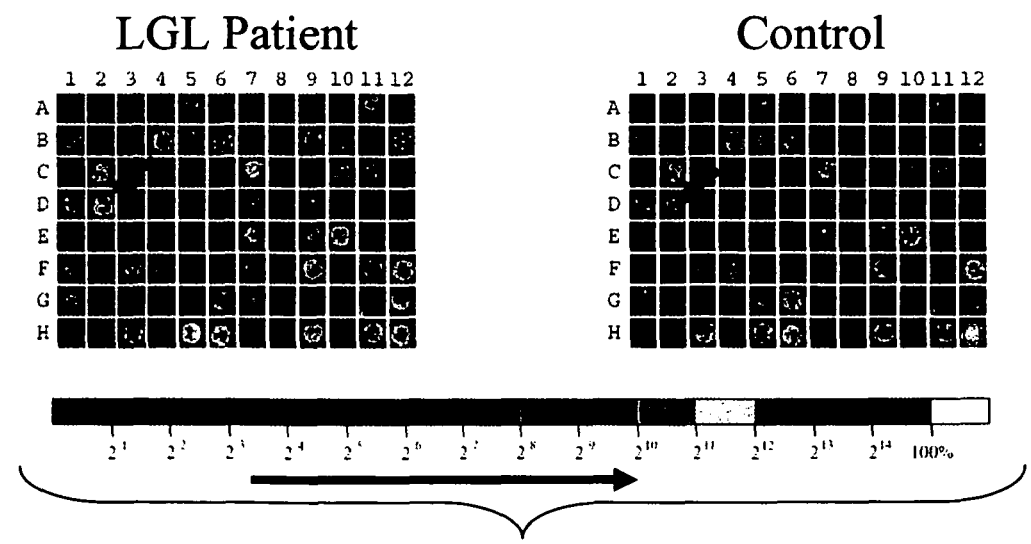
Figure 2A:
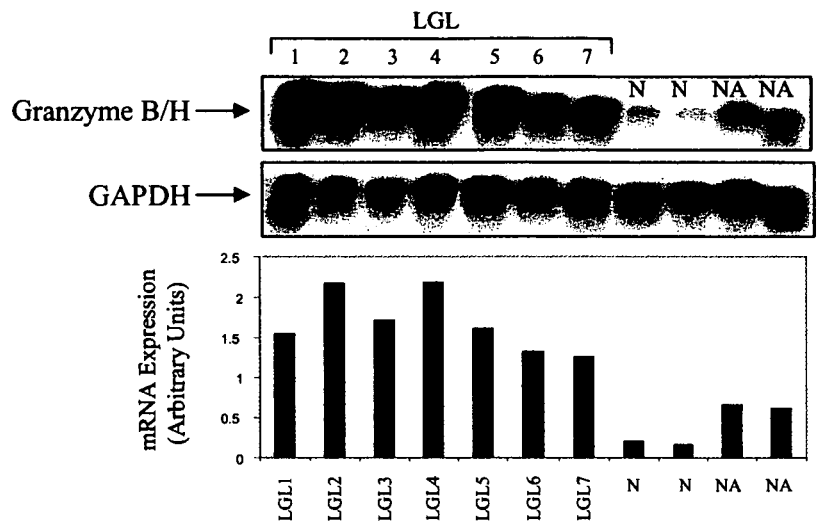
FIGS. 2A-2D show the Northern blot analysis of granzyme B/H, cathepsin W, perforin, and calpain. Northern blot analysis was performed with 10 μg of total RNA isolated from PBMC of leukemic patients and normal controls. Clones containing cDNA fragments were excised from the plasmids and used as probes. After hybridization with the corresponding gene probes, the Northern blots were stripped and reprobed with the housekeeping gene GAPDH and the bands were normalized using the ImageQuant program. LGL stands for LGL leukemia patients. N stands for normal. NA stands for normal. PBMC were activated by IL-2 and PHA as described in the Materials and Methods section.
Figure 2B:
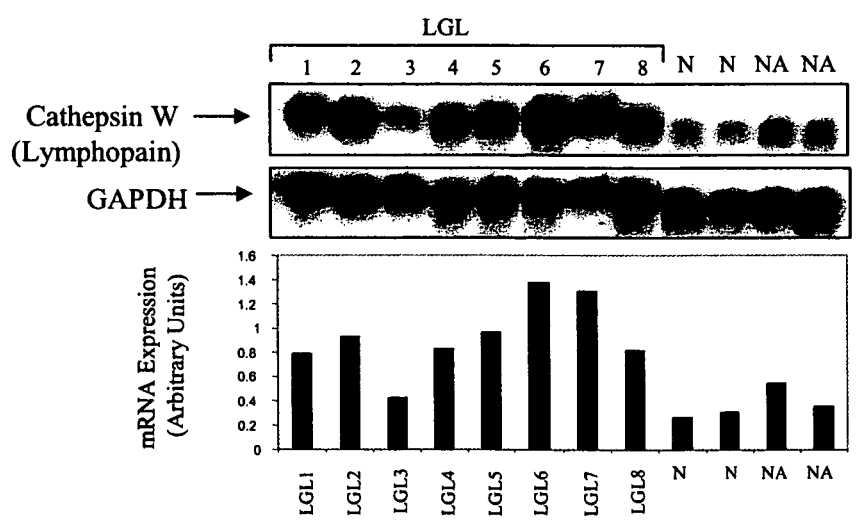
Figure 2C:
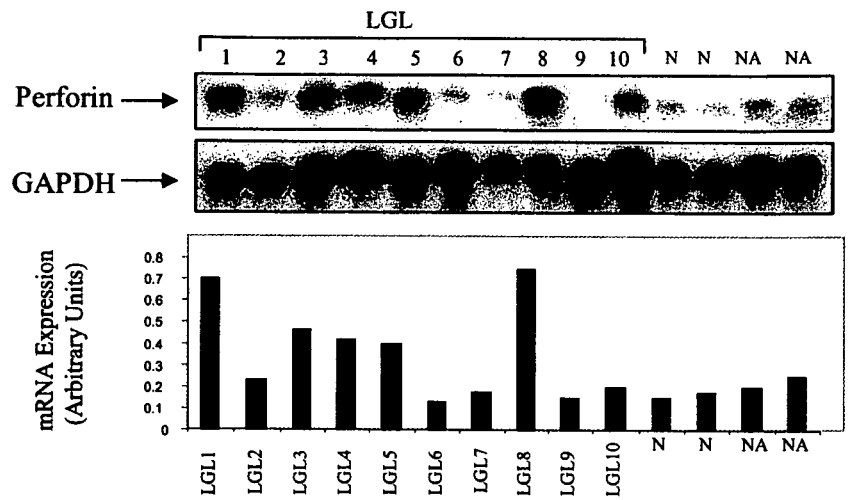
Figure 2D:
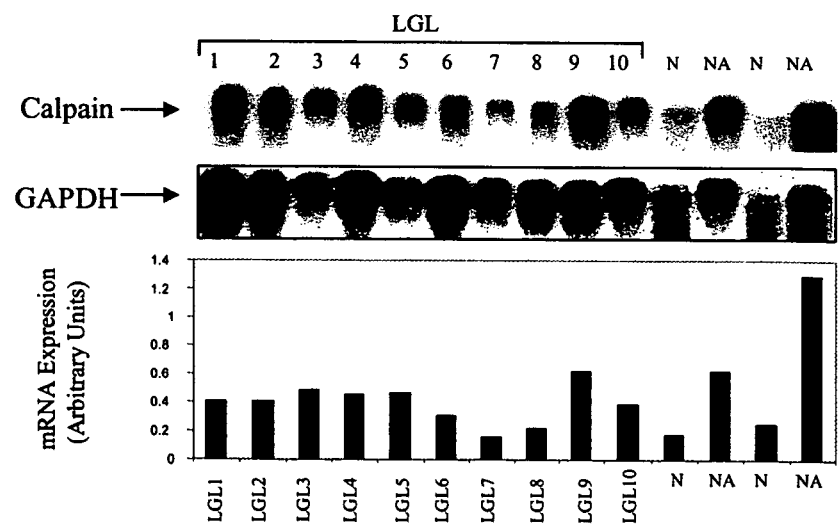

Overexpression of a variety cytotoxic genes was observed in leukemic LGL utilizing cDNA microarray from Incyte Genomics (FIG. 1 and Table 4). To verify the identity of these overexpressed genes, clones containing cDNA fragments of the selected genes were obtained from Incyte Genomics and confirmed by sequencing. Northern blots were then performed to confirm these results in samples from other LGL leukemia patients. For this analysis, we used the cDNA fragments (for the majority of the genes mentioned in the tables) obtained from the clones as probes (Incyte Genomics). All leukemic LGL showed constitutive expression of granzyme B and H, and cathepsin W (FIGS. 2A and 2B), whereas as a majority of patients showed overexpression of perforin (FIG. 2C). A gene coding for calpain small polypeptide was also expressed in the majority of the leukemic LGL (FIG. 2C). In addition to these cytotoxic genes, other genes were identified which were differentially expressed when comparing a sample from an LGL leukemia patient to a sample from a normal individual. Approximately 80 genes appeared upregulated and 12 downregulated in the cDNA microarray.

An Affymetrix chip was also used to identify differentially expressed genes in leukemic LGL. In these experiments, the expression of different genes was compared with normal PBMC, purified normal $CD8^+$ cells and leukemic LGL from two (2) patients. This analysis also showed the overexpression of genes coding for granzyme A, H, B, K and perforin. In addition, upregulation of cathepsin C (Table 5) was observed.

Figure 3A:
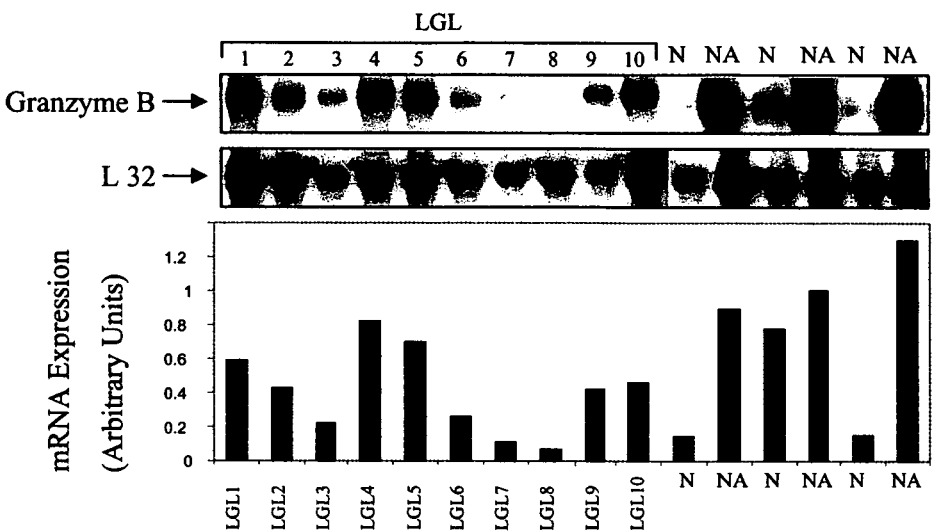
FIGS. 3A-3F show RNase protection assays. RNase protection assay (RPA) was performed as described in the Materials and Methods section. LGL stands for leukemic patients. N stands for normal. NA stands for normal activated. Bands showing the mRNA expression were quantitated and normalized with the housekeeping gene, L32, using ImageQuant program and relative expression was given as arbitrary units for each sample.
Figure 3B:
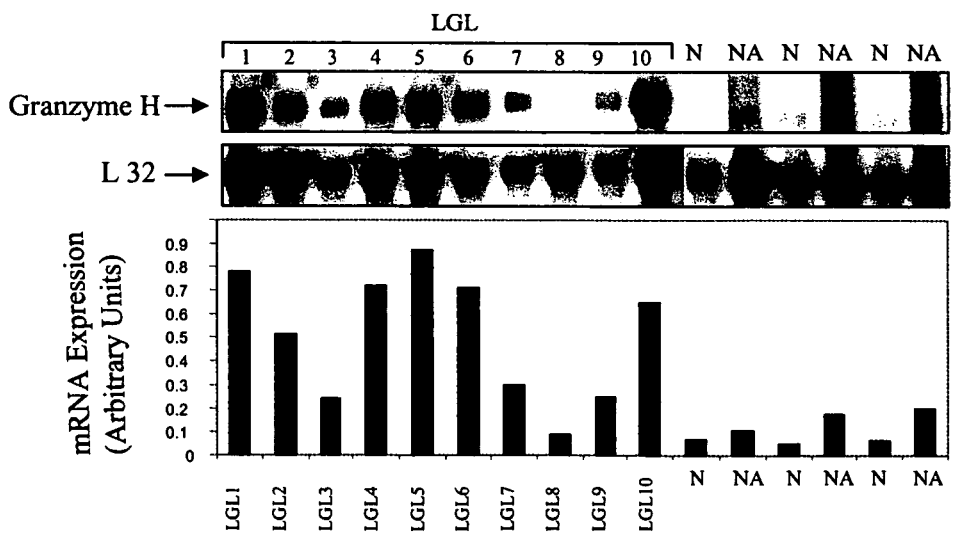
Figure 3C:
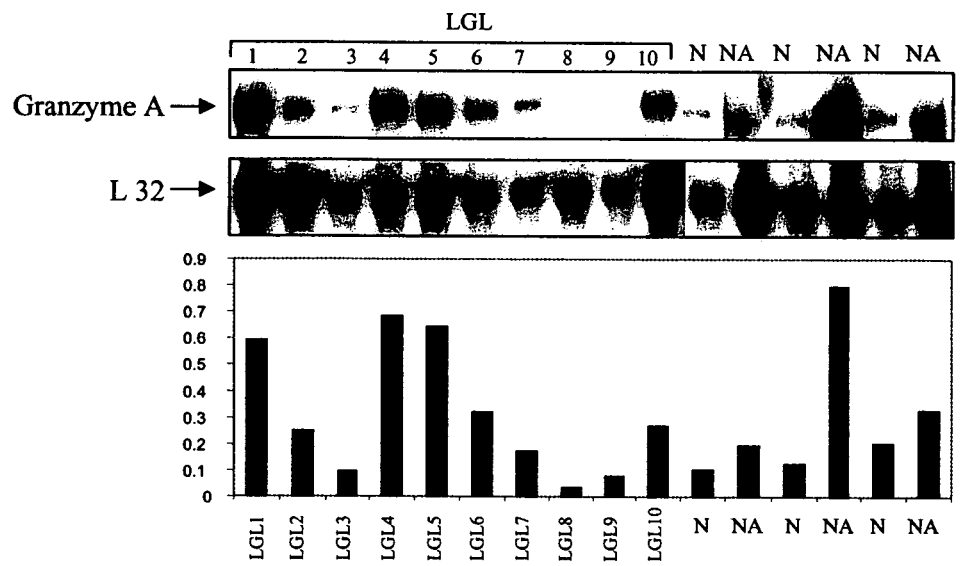
Figure 3D:
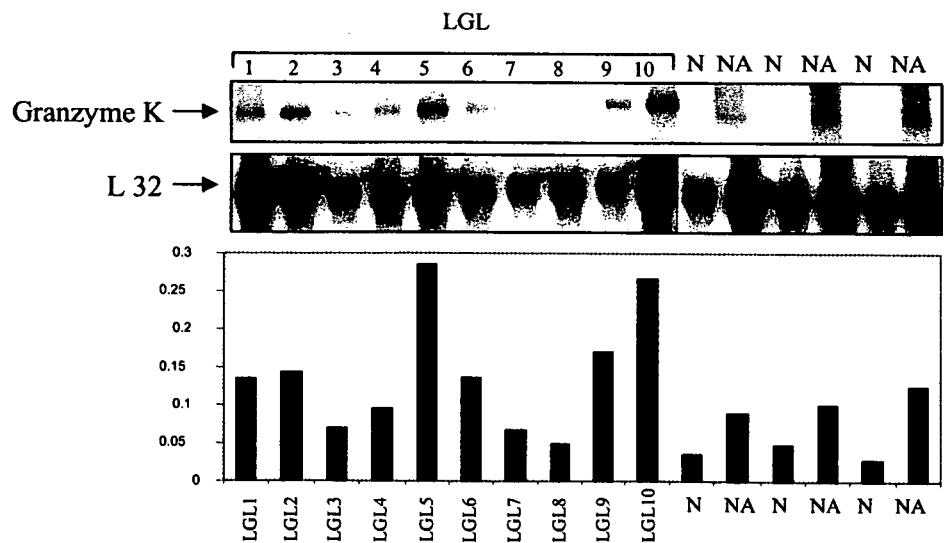
Figure 3E:
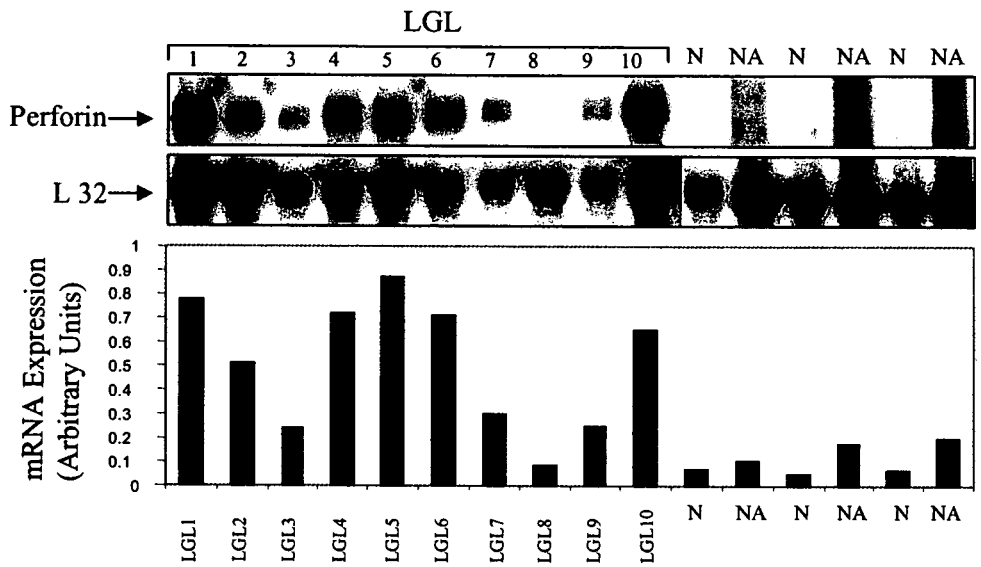
Figure 3F:
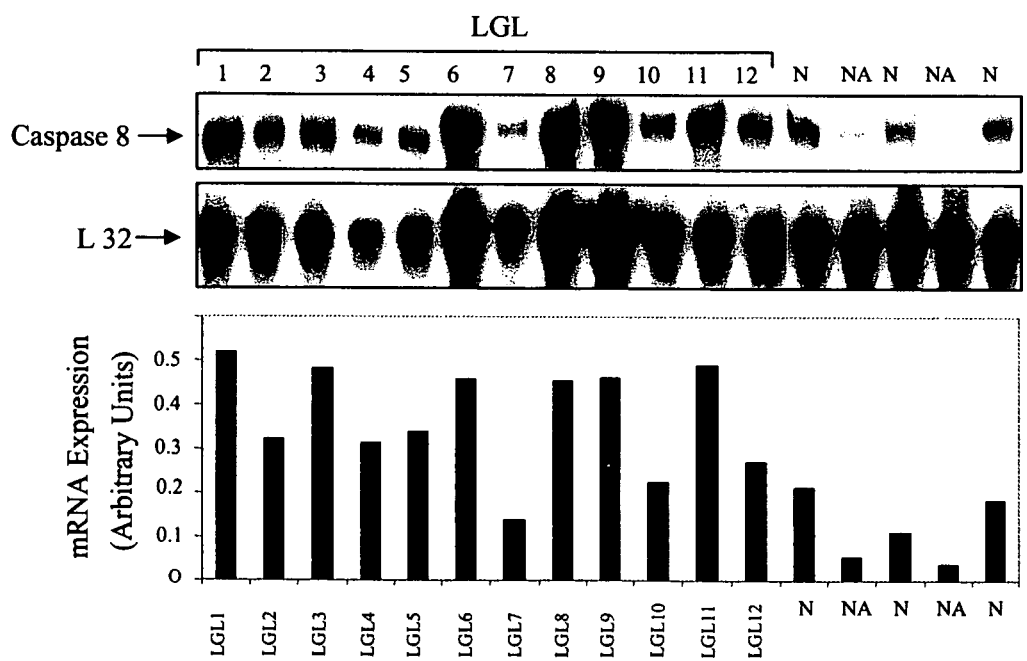
Figure 4:
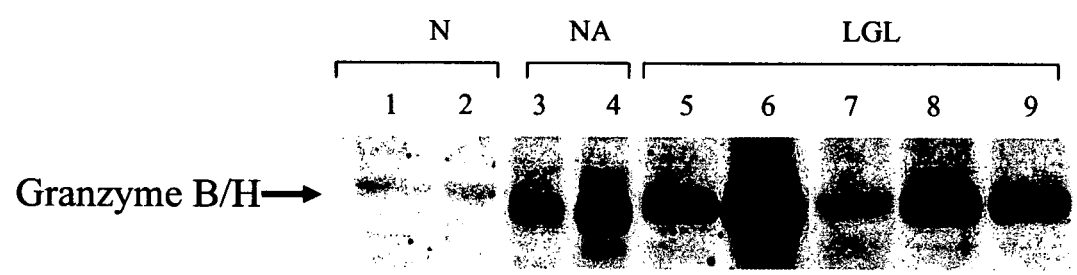
FIG. 4 shows the expression of granzyme H (B) in leukemic LGL. Western blot analysis of proteins isolated from normal, activated PBMC and leukemic LGL. Antibodies raised against granzyme B was used in this blot. Since granzyme B cross-react with granzyme H, it is difficult to distinguish between granzyme B and H. N stands for normal PBMC. NA stands for normal activated PBMC. LGL stands for leukemic LGL.

Protease inhibitors such as cystatin C, cystatin A, $\alpha$-1 antitrypsin and metalloproteinase inhibitor were downregulated in leukemic LGL when compared to normal PBMC. In $CD8^+$ cells, these inhibitors were drastically downregulated when compared to both normal PBMC and leukemic LGL (Table 6). Because of a high degree of sequence similarity, it was not possible to distinguish granzyme B from granzyme H in microarrays and in Northern blots. Therefore, an RPA was performed using specific probes for granzyme B and H. The majority of samples from the LGL leukemia patients constitutively overexpressed both granzyme B and H (FIGS. 3A and 3B). Granzyme B was also upregulated in activated PBMC, whereas such upregulation was not observed with granzyme H. Granzyme A and K were also overexpressed in the majority of the patient's samples (FIGS. 3C and 3D). RPA also confirmed the upregulation of perforin and caspase-8 in the majority of LGL patients (FIGS. 3E and 3F). Normal PBMC express low levels of caspase-8, but upon activation of PBMC with IL-2 and PHA, the message levels of caspase-8 were further reduced and in some cases hardly detectable. In Western Blot experiments, overexpression of granzymes in leukemic LGL (FIG. 4) was observed, although the antibody used in the experiment did not distinguish between granzyme B and granzyme H.

EXAMPLE 2

CC and CXC Chemokine Expression: LGL Leukemia Samples Constitutively Express High Levels of RANTES, MIP-1B and IL-8

Figures 6A, 6B:
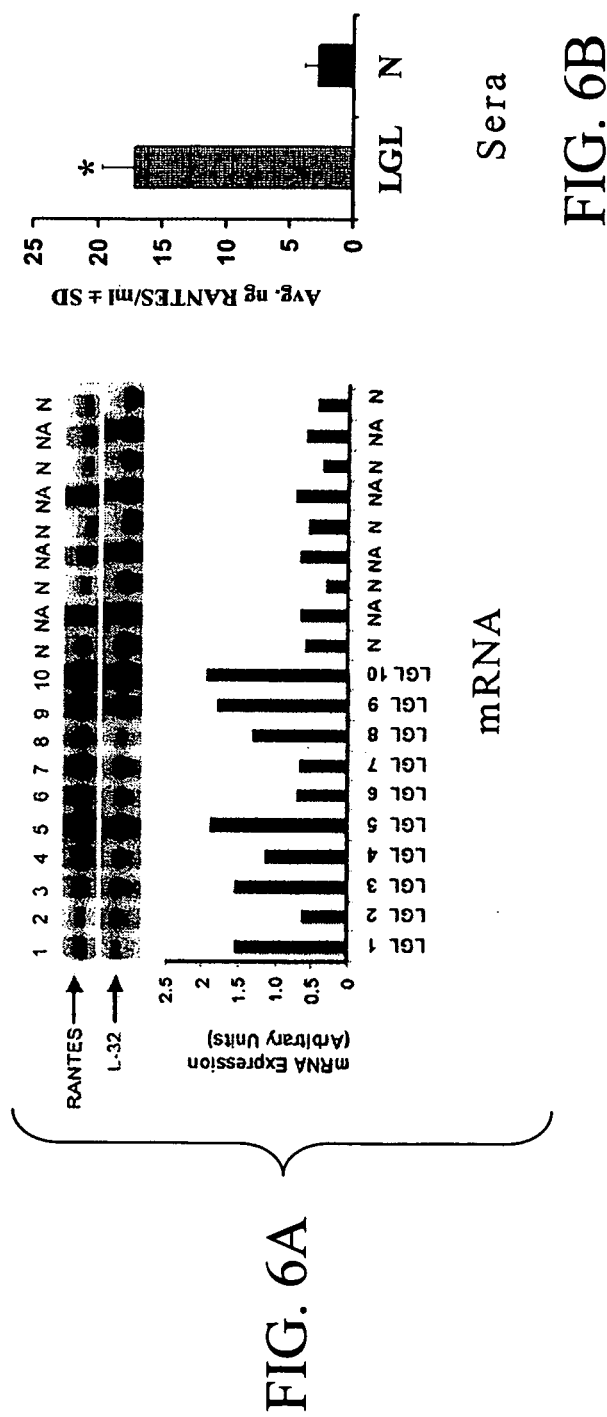
FIGS. 6A and 6B show overexpression of RANTES in LGL leukemia. RNase protection assays (RPA) were performed as described in the Materials and Methods section (FIG. 6A). LGL: LGL leukemia cells, N: normal cells, NA: activated normal cells. Bands showing the mRNA expression were quantified and normalized with the housekeeping gene L32. Relative expression was given as arbitrary units for each sample. 10 LGL leukemia samples and 5 normal samples were used for statistical analysis. T-tests were performed assuming unequal variances. The P value obtained for RANTES was $p<0.01$.
Figure 8A:
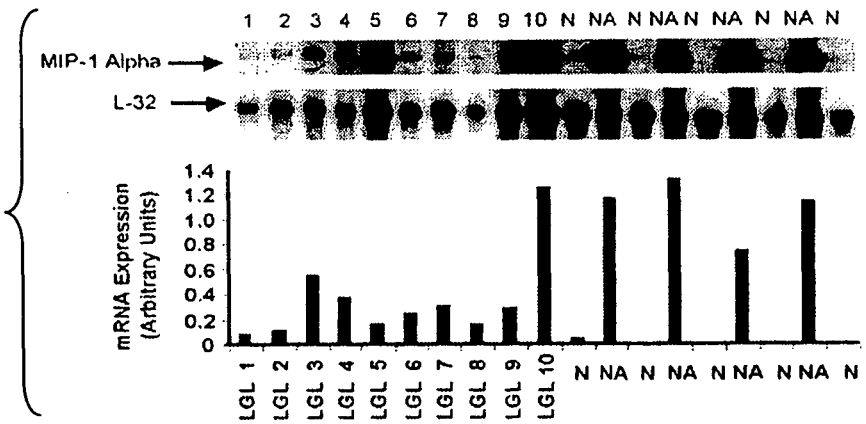
FIGS. 8A-8C show increased expression of MIP-1α, IL-1β, and IL-1Ra transcripts in LGL leukemia. RPAs were performed as described in the Materials and Methods section. Bands corresponding to mRNA expression were quantified and normalized with the housekeeping gene, L32, using ImageQuant. Relative expression was given as arbitrary units for each sample. LGL: leukemia cell LGL, N: normal cells, NA: activated normal cells.
Figure 8B:
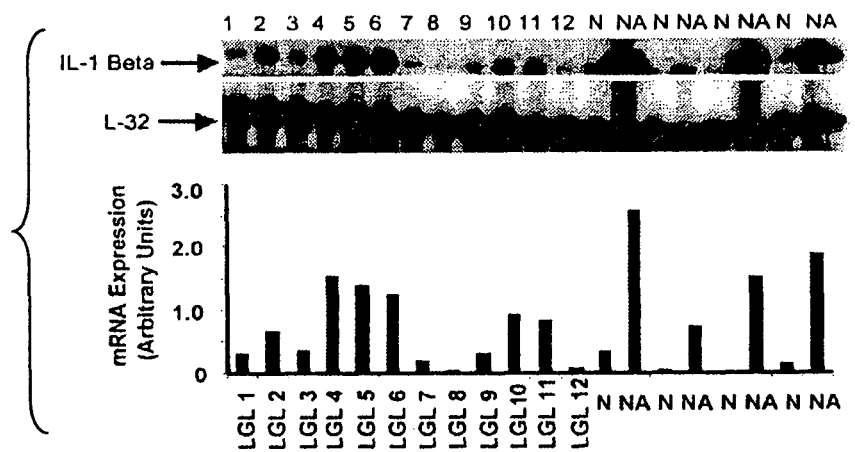
Figure 8C:
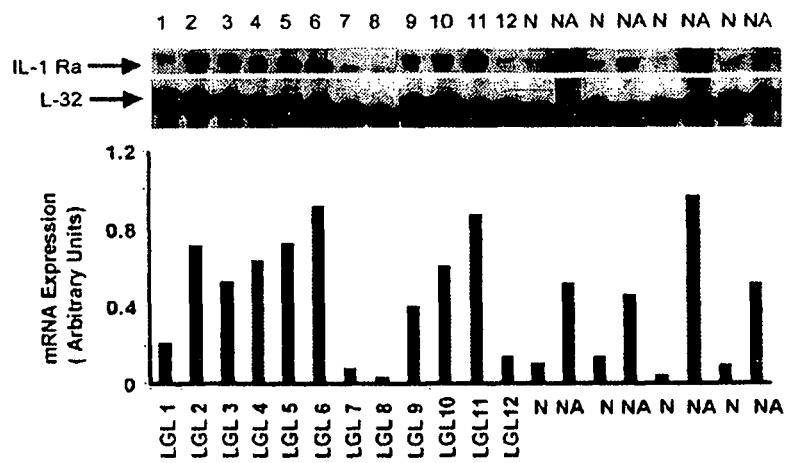
Figure 9A:
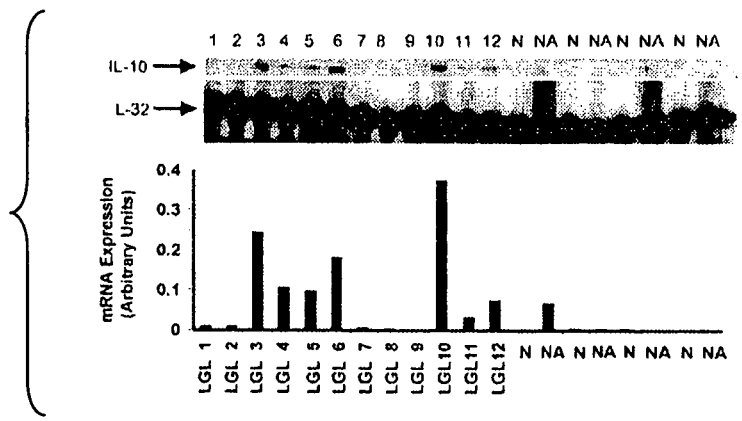
FIGS. 9A-9C show elevated IL-10, IL-12p35, and IL-8 mRNA expression in LGL leukemia. RPAs were performed as described in the Materials and Methods section. Bands identified as IL-10 mRNA were quantified and normalized with the housekeeping gene, L32, using an ImageQuant program. LGL: leukemic LGL, N: normal PBMCs, NA: normal activated PBMCs. Relative expression was given as arbitrary units for each sample.
Figure 9B:
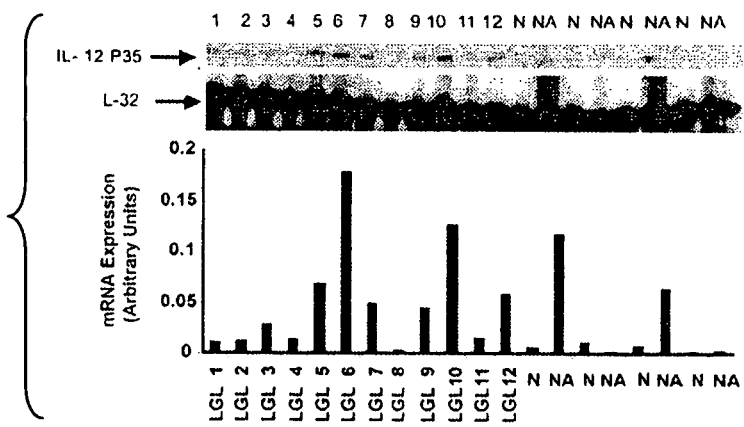
Figure 9C:
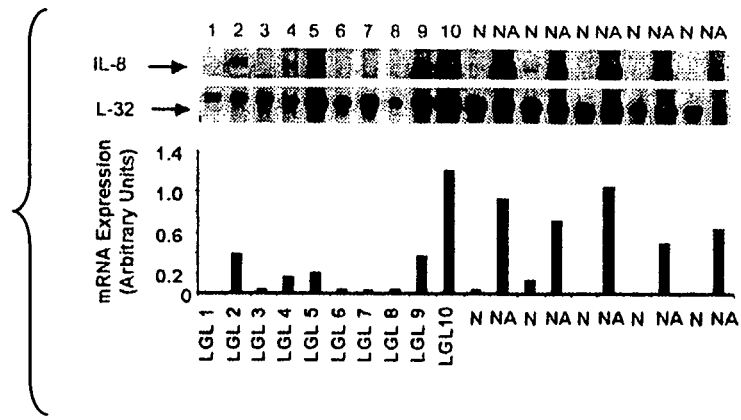
Figure 10A:
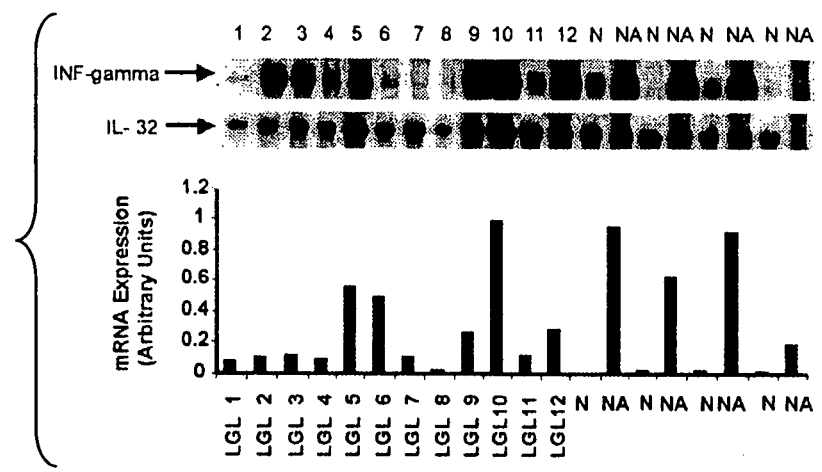
FIGS. 10A and 10B show elevated levels of IL-18 and IFNγ mRNA expression in LGL leukemia. RPAs were performed as described in the Materials and Methods section. Bands corresponding to IFNγ mRNA were quantified and normalized with the housekeeping gene, L32, using ImageQuant. Relative expression was given as arbitrary units for each sample. LGL: leukemic LGL, N: normal PBMCs, NA: normal activated PBMCs.
Figure 10B:
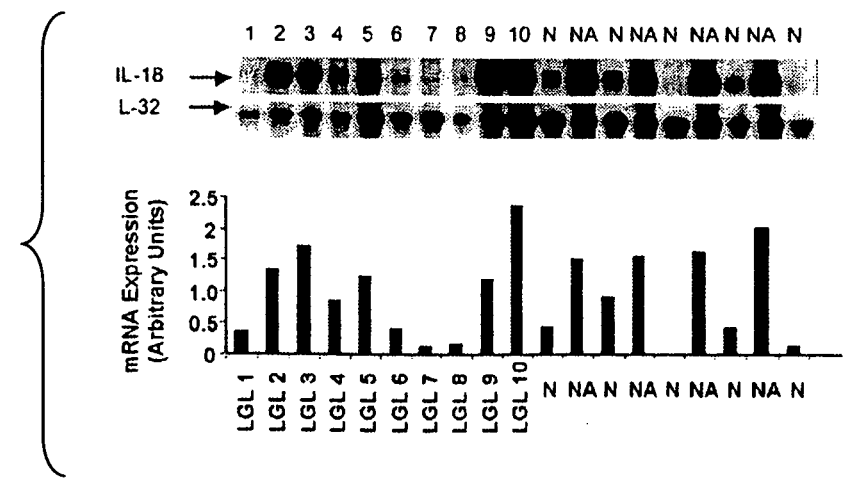

Protein arrays for 20 LGL leukemia sera and 6 sets of pooled normal sera were completed in duplicate. The most commonly elevated cytokines belonged to the CC chemokine family including RANTES, MIP-1β and IL-8 (FIG. 5). Significant overexpression of RANTES (FIG. 6A), MIP-1β transcripts (FIG. 7A) and macrophage inflammatory protein-1α (MIP-1α) (FIG. 8A) in leukemic LGL samples was observed. Elevated levels of IL-8 mRNA were found in some samples from patients with LGL leukemia (FIG. 9C) and as a group achieved borderline significance (P<0.055). ELISA data further confirmed the elevated expression of RANTES, MIP-1β, and IL-8 proteins in LGL leukemia sera (FIGS. 6B and 7B and Table 7). While the mean RANTES levels for normal sera (N) as detected by the ELISA reagents was approximately 3 ng/ml, RANTES levels in patient sera (LGL) ranged from 14 ng/ml to 20 ng/ml with a mean level of 17 ng/ml. ELISA testing revealed that MIP-1β secretion was significantly elevated in 16 of the 27 LGL leukemia sera (FIG. 7B). Sera from LGL leukemia patients had significantly elevated IL-8 levels compared to normal sera due to the greatly increased amounts of IL-8 in 11 of the 27 sera tested (Table 7). In contrast to these findings, ELISA analysis for MIP-1α could not validate the RPA analysis showing increased levels of MIP-1α transcripts in each of 10 LGL leukemia patient samples. Of interest, densitometry analyses of the protein arrays had revealed that 6 of 20 LGL leukemia sera contained significantly elevated levels of MIP-1α. The ELISA results utilizing a larger number (27) of LGL leukemia samples showed that sera from 5 patients demonstrated significantly elevated amounts of this chemokine. Thus, the mean MIP-1α levels were not increased in sera from LGL leukemia patients compared to normal control sera (Table 7).

EXAMPLE 3

Increased Levels of Other Cytokines in LGL Leukemia (IL-18, IL-RA)

Levels of expression of a large number of cytokine gene transcripts were found not to be elevated in LGL leukemia samples by RPA include lymphotactin (Ltn), monocyte chemoattractant protein-1 (MCP-1), interleukin-1α (IL-1α), interleukin-4 (IL-4), interleukin-5 (IL-5), interleukin-6 (IL-6), interleukin-9 (IL-9), interleukin-14 (IL-14), interleukin-15 (IL-15) and tumor necrosis factor-α (TNF-α) (not shown). In contrast RPA results showed significantly increased levels of IL-1β, IL-1Ra, interleukin-10 (IL-10), interleukin-12 (IL-12), IL-18, interferon gamma (INF-γ) gene transcripts in these patient samples (FIGS. 8A-8C, FIGS. 9A-9C, and FIGS. 10A-10B). ELISA testing was then performed for each of these proteins, except for IL-10 and IL-12 as protein array testing did not detect increased levels of these proteins in LGL sera. Of note protein array testing showed overexpression of IL-1β in only 4 of 20 LGL leukemia samples. However, IL-1β ELISA testing was performed since a previous report utilizing both microarray and ELISA had suggested increased levels of this cytokine in a small group of patients with LGL leukemia. Although the IL-1β transcripts were elevated, the IL-1β protein levels in the LGL leukemia sera were not different than levels seen in normal sera.

Levels of IL-18, IL-1Ra, IFN-γ, and TNF-α were elevated in LGL leukemia patient samples to varying extents (Table 7) was demonstrated. Mean levels of IL-18 and IL-1Ra were significantly higher in LGL leukemia sera than normal sera. Although mean levels of INF-γ and TNF-α were not elevated, sera from 11 and 13 patients respectively did show increased levels of these cytokines.

EXAMPLE 4

Other Protein Array Results

Many other growth factors or chemokines/lymphokines, not tested by RPA, were not differentially expressed when comparing results of twenty LGL leukemia sera to six sets of pooled normal sera utilizing the protein array. Such proteins included epithelial cell-derived neutrophil attractant-78 (ENA-78), granulocyte colony-stimulating factor (G-CSF), granulocyte monocyte-colony stimulating factor (GM-CSF), growth-regulated oncogene (GRO), growth-regulated oncogene-alpha (GRO alpha), IL-2, interleukin-3 (IL-3), interleukin-7 (IL-7), interleukin-13 (IL-13), monocyte chemoattractant protein-2 (MCP-2), monocyte chemoattractant protein-3 (MCP-3), macrophage colony-stimulating factor (MCSF), macrophage-derived chemokine (MDC), monokine induced by interferon-gamma (MIG), stem cell factor-1 (SCF-1), stromal cell-derived factor-1 (SDF-1), thymus- and activation-regulated chemokine (TARC), tumor growth factor-beta (TGF-β) epidermal growth factor (EGF), insulin-like growth factor 1 (IGF-1) and thrombopoitin (TPO). There was a suggestion that there might be elevated levels of endothelial or blood vessel growth factors as evidenced by increased angiotensin (ANG), vascular endothelial growth factor (VEGF) and platelet-derived growth factor (PDGF) expression in at least in five of 20 LGL leukemia sera. Similar results were also found for leptin-I-309 and oncostatin M (OSM).

It should be understood that the examples and embodiments described herein are for illustrative purposes only and that various modifications or changes in light thereof will be suggested to persons skilled in the art and are to be included within the spirit and purview of this application.

TABLE 1

Differentially expressed genes in LGL1 and LGL2. This data is based on Incyte Genomics and Affymetrix Chip FL 6800

| Gene Name | Incyte Genomics BDE (p1/p2) | GenBankID | Affymetrix Fold Change (LGL1/LGL2) | GenBank ID If different from Incyte Genomics |
|---|---|---|---|---|
| Upregulated Genes Proteolytic enzymes | | | | |
| Granzyme H precursor | 6.3 (3332/533) | M57888 | (1.5/1.8) (21.8/10.8) | M37245 M28879 |
| Lymphopain (CathapsinW) | 5.4 (3578/658) | AF013661 | — | |
| Perforin | 3.8 (1549/413) | L40557 | (103–44.7) | M31951 |
| Matrix metalloprotenase 8 (neutrophil collagenase) | 3.2 (1178/370) | J05556 | (1.0/−1.1) | |
| Calpain, small polypeptide | 2.0 (4089/2059) | X04106 | (1.1/1.3) | |
| Granzyme A | 1.9 (1944/1022) | NM06144 | — | |
| Caspase 8 (From RPA also) | 1.4 (2035/1480) | U97075 | (1.2/−1.4) | AF005775 |
| Inducible or regulated proteins | | | | |
| Interferon regulated factor 4 | 5.0 (1128/226) | U52682 | (6/−1.5) | |
| TNF-α induced protein A 20 | 3.2 (1507/470) | M59465 | (−1.3/−3.8) | |
| Heat shock 70 kd protein 5 (Glucose regulated protein 78 kd) | 2.8 (4090/1464) | X87949 | (5.3/14.5) | M11717 |
| RANTES (RPA also) | 2.7 (2490/909) | M21121 | (5.9/6) | |
| Human rap 2 mRNA for ras related proteins | 2.6 (899/327) | X12534 | — | |
| p53 inducible proteins | 2.2 (2040/916) | L47738 | (2.9/2.3) | |
| Glucose regulated proteins 58 kd | 2.2 (3661/1641) | AL043206 | — | |
| receptors RECEPTORS | | | | |
| CD8 antigen, alpha polypeptide (p32) | 7.3 (4325/594) | M12824 | (−1.2/−1.1) | M27161 |
| Killer cell lectin-like receptor subfamily C, member 2 (NKG2-CII) | 5.5 (2115/383) | AJ001684 | | |
| CD8 antigen beta polypeptide (p37) | 9.0 (1953/401) | NM004931 | (7.2/5.2) | X13444 |
| Musculin (activated B-cell factor-1) | 4.1 (466/113) | AF087036 | | |

TABLE 1-continued

Differentially expressed genes in LGL1 and LGL2. This data is based on Incyte Genomics and Affymetrix Chip FL 6800

| Gene Name | Incyte Genomics BDE (p1/p2) | GenBankID | Affymetrix Fold Change (LGL1/LGL2) | GenBank ID If different from Incyte Genomics |
|---|---|---|---|---|
| Killer cell lectin-like receptor subfamily C, member 3 (NKG2-CII) | 3.8 (1335/344) | AJ001685 | | |
| subfamily C, member 2 (NKG2-CII) | 5.5 (2115/383) | AJ001684 | | |
| CD8 antigen beta polypeptide (p37) | 4.9 (1953/401) | X13444 | (7.2/5.2) | |
| Musculin (activated B-cell factor-1) | 4.1 (466/113) | AF060154 | | |
| Killer cell lectin-like receptor Low affinity immunoglobulin Gamma FC receptor III-1 precursor | 3.9 (1335/344) | J04162 | (8.1/6.8) | |
| Filamin I (actin-binding protein-280) | 3.8 (1085/287) | X53416 | (2.1/1.9) | |
| Lectin-like Type II integral Membrane protein (NKG2-E) | 3.8 (1300/344) | AJ001685 | | |
| Natural Killer cells group 7 | 3.1 (11251/3591) | S69115 | (9.3/9.1) | |
| Protein tyrosine phosphatase type J receptor | 2.1 (4614/2177) | L05148 | (2.9/2.6) | |
| Delta sleep inducing peptide Immunoreceptor | 2.3 (5424/2319) | BE295817 | | |
| Lymphotoxin-Beta receptor precursor | 2.3 (3587/1544) | AI271415 | | |
| MHC class II, DR beta 5 receptor | 2.4 (2264/953) | X00700 | | |
| NKG2-D type II integral membrane protein | 2.1 (1019/494) | X54870 | (7.3/9.4) | |
| Protein tyrosine phosphatase Non-receptor type 12 | 2.1 (1036/494) | M93425 | (1.6/1.0) | |
| Leukemia virus receptor (CGLVR1) | 2.1 (713/340) | L20859 | (2.9/2.5) | |
| Kinases and Phosphatases | | | | |
| Dual specificity Phosphatase-1 (PAC-1) | 4.2 (2484/585) | L11329 | (1.6/1.2) | |
| Dual specificity Phosphatase-5 | 2.7 (857/320) | U10886 | (1.1/1.6) | |
| Tyrosine protein tyrosine phosphatase | 2.6 (713/272) | U15932 | (1.2/2.3) | |
| Protein Kinase C etc | 2.2 (2780/1239) | M55284 | — | |
| Zeta Chain (TCR) associated protein kinase (70 kd) | 2.1 (4614/2177) | L05148 | (2.9/2.6) | |
| Src Kinase-associated phosphoprotein of 55 kd | 2.1 (730/327) | Y11215 | (3.3/2.4) | |
| Phosphatidyl inositol (4,5,bisphosphatase5-phosphatase homolog | 2.1 (764/372) | 638789 | — | |
| Protein phosphatase 2. Regulated subunit B (B56) | 2.0 (1071/526) | U37352 | (6.8/5.8) | |

TABLE 1-continued

Differentially expressed genes in LGL1 and LGL2. This data is based on Incyte Genomics and Affymetrix Chip FL 6800

| Gene Name | Incyte Genomics BDE (p1/p2) | GenBankID | Affymetrix Fold Change (LGL1/LGL2) | GenBank ID If different from Incyte Genomics |
|---|---|---|---|---|
| Protein Phosphatase 1, (catalytic subunit, alpha isoform) | 2.0 (1643/835) | J04759 | | |
| Transcription Factors | | | | |
| Runt related transcription factors 3 | 3.5 (2689/775) | D43968 | (3.8/3.5) | |
| Miscellaneous | | | | |
| EST.1 | 17.7 (346/189) | H06366 | | |
| EST.2 | 11.8 (2571/218) | AA482549 | | |
| EST.3 | 3.0 (544/182) | N47089 | | |
| Solute carrier protein | 4.6 (785/172) | L14595 | (1.4/1.6) | |
| Filamin A alpha | 3.8 (1085/287) | X53416 | (2.1/1.9) | |
| Hemoglobin delta | 3.1 (2084/667) | V00505 | | |
| Hemoglobin beta | 3.0 (4319/1419) | V00497 | | |
| KIAA 0668 protein | 2.6 (3476/1254) | AB014568 | | |
| MHC, Class II DR beta 3 | 2.4 (2264/953) | X00700 | | |
| PLECKSTRIN | 2.4 (2033/854) | X07743 | (2.0/2.4) | |
| Isocitrate dehydrogenase 2 (NADP+) Mitochondrial | 2.2 (2067/893) | X69433 | (2.2/2.7) | |
| Putative translation initiation factor | 2.0 (4003/2046) | L26247 | (−1.3/−1.5) | |
| Tubulin, Beta polypeptide | 2.0 (2640/1349) | AW163523 | | |
| Ubiquitin B | 1.9 (5668/3024) | BE250544 | | |
| Moesin | 1.8 (5015/2750) | Z98946 | | |
| Nuclear factor of activated T cells, cytoplasmic | 1.8 (2586/1440) | U85430 | (1.8/2.9) | |
| Ubiquitin C | 1.7 (3568/2071) | AA600188 | | |
| GTP binding protein, alpha 13 | 1.8 (2147/1195) | U87964 | (−1.3/−1.5) | |
| Calriticulin Precursor | 2.2 (3101/1384) | M84739 | (2.0/2.2) | |
| KIAA0158 gene complete CDs | 3.9 (2953/753) | 063878 | | |
| Hemoglobin alpha I | 3.2 (1074/333) | V00491 | | |
| T cell receptor gamma chain | 3.1 (987/315) | M30894 | (5.0/11.3) | |
| FYN Oncogene related to SRC FGR, YES | 3.x (3405/313) | Z97989 | | |
| EB1 mRNA | 2.4 (1075/442) | U24166 | (−1.8/−2) | |
| PLECKSTRIN | 2.4 (2033/854) | X07743 | | |
| DNAJ protein Homolog | 2.4 (237/1065) | D85429 | (1.4/−1.7) | |
| MHC Class II HLA-DRW 10 beta | 2.4 (2264/953) | D85429 | | |
| Lymphotoxin-beta receptor precursor | 2.3 (3587/1544) | L04270 | | |
| Leucine Zipper Protein | 2.3 (5424/2319) | Z50781 | (1.4/−2.7) | |
| Probable protein disulfide Isomerase ER-60 precursor | 2.2 (3661/1641) | Z49835 | (1.4/1.0) | |
| Troponin T, Fast skeletal muscle | 2.2 (1628/743) | M21984 | | |
| Isomerase beta Transforming growth factor receptor III | 3.7 (764/204) | L07594 | (10.6/7.1) | |
| DEC1, complete cds | 3.5 (1498/1429) | AB004066 | | |
| Granulocyte Colony-stimulating Factor induced gene | 3.1 (11251/3591) | S65115 | (9.3/9.1) | |

TABLE 1-continued

Differentially expressed genes in LGL1 and LGL2. This data is based on Incyte Genomics and Affymetrix Chip FL 6800

| Gene Name | Incyte Genomics BDE (p1/p2) | GenBankID | Affymetrix Fold Change (LGL1/LGL2) | GenBank ID If different from Incyte Genomics |
|---|---|---|---|---|
| Integrin, beta 2 | 2.7 (3718/1377) | M15395 | | |
| Clone 23912 | 2.6 (3476/1341) | AF038178 | | |
| Putative tumor suppressor Protein (RDA32) | 2.5 (1145/453) | AF061836 | | |
| Down regulated genes | | | | |
| *Homo sapiens* Indian hedgehog protein (IHH) | −18.6 (477/7779) | L38517 | (−1.6/−1.1) | |
| CD20 Receptor | −16.2 (229/3703) | X07203 | (1.1/−1.9) | |
| Human germline IgD chain gene, C-region | −11.0 (210/2313) | K02882 | (−9.5/−7.5) | |
| Human transporter Protein (g17) | −10.4 (300/3124) | U49082 | (−2/−1) | |
| Ribosomal protein S26 | −6.2 (321/1853) | X69654 | (−3.1/1.1) | |
| EST | −3.4 (429/1371) | R85437 | | |
| CD 72 antigen | −3.3 (353/1165) | M54992 | (1.3/1.7) | |
| EST | −2.5 (629/1583) | AA916867 | | |
| Endothelial differentiation protein (Edg-1) | −2.5 (447/1033) | M31210 | (−2.6/−5.2) | |
| Diacylglycerol kinase, alpha (80 kD) | −2.5 (883/2172) | X62535 | (−1.4/−2.3) | |
| 60S Ribosomal protein L41 | −2.3 (5372/2339) | Z12962 | (−1.2/−1.2) | |
| EST | −2.3 (708/1616) | AA134589 | | |

TABLE 2

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| perforin | 32904_at | 72.8 | 39.5 | 45.4 | 8.5 |
| serine protease | 40078_at | 55.7 | 48.7 | 38.7 | 3.0 |
| mast cell function-associated antigen homolog (MAFA) | 34975_at | 55.2 | 45.4 | 61.1 | 16.2 |
| NK-receptor (NK-p46) | 34039_at | 53.6 | 45.2 | 50.6 | 7.8 |
| gb = W28589 | 40913_at | 47.7 | 41.2 | 44.2 | 23.9 |
| suppressor related (DOC-1R) | 35151_at | 45.3 | 40.1 | 27.0 | 42.8 |
| ribosomal protein S6 kinase 1 (RPS6KA1) | 1127_at | 42.4 | 40.0 | 50.6 | 2.2 |
| butyrophillin (BT3.3) | 38759_at | 37.8 | 33.3 | 52.9 | 17.8 |
| CD94 | 33531_at | 35.2 | 34.2 | 17.9 | 7.3 |
| MEGF9 | 36488_at | 34.1 | 44.6 | 33.4 | 10.3 |
| chronic granulomatous disease protein | 40159_r_at | 33.7 | 83.5 | 63.5 | 8.8 |
| gamma2-adaptin (G2AD) | 38799_at | 30.3 | 29.2 | 27.5 | 40.5 |
| calcineurin A2 | 39780_at | 29.0 | 17.4 | 15.2 | 19.0 |
| beta adaptin | 36161_at | 28.4 | 21.1 | 11.5 | 26.7 |
| G protein-coupled receptor V28 | 40646_at | 27.4 | 40.3 | 25.1 | 5.1 |
| thrombin receptor | 41700_at | 22.5 | 8.3 | 14.2 | 4.8 |
| GTPase-activating protein | 36843_at | 22.1 | 9.1 | 19.5 | 12.2 |
| SH3 domain containing adaptor protein (SCAP) | 34432_at | 21.9 | 10.4 | 22.8 | 10.3 |
| AML1c | 39421_at | 21.8 | 17.2 | 31.7 | 10.6 |
| KIAA0664 protein | 34259_at | 21.7 | 38.4 | 27.0 | 18.0 |
| gb = AA978353 | 41126_at | 21.4 | 8.8 | 13.9 | 1.4 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| Matk = megakaryocyte-associated tyrosine kinase | 36264_at | 20.7 | 17.1 | 13.1 | 1.4 |
| vascular smooth muscle alpha-actin | 32755_at | 20.1 | 27.8 | 22.0 | 3.8 |
| lysyl hydroxylase (PLOD) | 36184_at | 19.8 | 18.0 | 9.8 | 1.1 |
| candidate tumor suppressor gene 21 protein isoform I | 40497_at | 19.7 | 16.1 | 26.6 | 13.1 |
| beta2-syntrophin (SNT B2) | 40589_at | 19.2 | 22.3 | 22.1 | 13.1 |
| hexokinase III (HK3) | 36372_at | 18.8 | 39.6 | 4.1 | 6.7 |
| telomeric repeat DNA-binding protein (PIN2) | 1329_s_at | 17.3 | 12.9 | 14.3 | 13.8 |
| cytotoxic T-lymphocyte-associated serine esterase 1 (CTLA1) | 32370_at | 17.3 | 12.1 | 9.8 | 1.6 |
| T cell-specific protein (RANTES) | 1404_r_at | 17 | 10.2 | 18.3 | 4.5 |
| CMRF-35-H9 | 41059_at | 16.8 | 21.0 | 15.6 | 5.7 |
| Human immune interferon (IFN-gamma) | 1021_at | 16.7 | 21.7 | 18.8 | −2.1 |
| placenta (Diff48) | 32978_g_at | 16.5 | 14.4 | 6.9 | 23.7 |
| medium-chain acyl-CoA dehydrogenase (MCAD) | 37532_at | 16.4 | 15.1 | 18.6 | 28.3 |
| mRNA for YSK1 | 40104_at | 16.3 | 12.5 | 13.2 | 19.1 |
| m6A methyltransferase (MT-A70) | 32245_at | 16.2 | 16.4 | 19.8 | 27.4 |
| CD3G gene, exon 1 | 39226_at | 16.2 | 6 | 5.3 | 3.4 |
| PUTATIVE novel protein similar to many (archae)bacterial, worm and yeast hypothetical proteins | 41249_at | 15.8 | 27.6 | 27.5 | 8.2 |
| gb = AI004207 | 36732_at | 15.8 | 25.1 | 17.6 | 22.2 |
| microsomal glutatilone S-transferase 3-(MGST3) | 39018_at | 15.6 | 21.8 | 16.9 | 28.4 |
| similar to mouse Choline/Ethanolamine Kinase (O55229) | 32033_at | 15.6 | 14.4 | 13.6 | 25.3 |
| 26S proteasome subunit p40.5 | 32211_at | 15.3 | 15.2 | 11.7 | 12.7 |
| Fc-gamma RIII-1 | 31499_s_at | 15 | 5.8 | 5.4 | −4.1 |
| gb = AF070644 | 38652_at | 14.6 | 16.6 | 14.4 | 8.4 |
| gb = U79260 | 37242_at | 14.5 | 15.9 | 11.5 | 17.5 |
| Ste = 20 related kinase SPAK | 40986_at | 14.5 | 10.9 | 18.2 | 8.2 |
| Guanine Nucleotide-Binding Protein Rap2 | 1819_at | 14.5 | 5.8 | 6.5 | 4.1 |
| SCA1 mRNA for ataxin | 36142_at | 14.2 | 13.2 | 16.9 | 7.7 |
| butyrophilin (BTF4) | 38760_f_at | 14.2 | 13.3 | 18.7 | 7.1 |
| HBV associated factor (XAP4) | 32202_at | 14.0 | 16.2 | 10.9 | 12.5 |
| leukocystatin | 34965_at | 13.9 | 8.2 | 12.1 | 2.6 |
| vav oncogene | 1919_at | 13.9 | 15.6 | 19.2 | 3.5 |
| beta-2-adrenergic receptor | 610_at | 13.9 | 9.1 | 15.9 | 3.6 |
| DNA from chromosome 19p13.2 cosmids R31240, R30272 and R28549 containing the EKLF, GCDH, CRTC, and RAD23A genes | 1751_g_at | 13.9 | 17.2 | 10.9 | 23.2 |
| DNA sequence from PAC 66H14 on chromosome 6q21–22. Contains FYN (P59-FYN, SYN, SLK) gene coding for two isoforms | 40479_at | 13.4 | 11.0 | 16.4 | 13.5 |
| transcription factor LSF | 40084_at | 13.3 | 12.3 | 11.3 | 11.7 |
| rap2 | 41318_g_at | 13.2 | 3.3 | 5.9 | 2.8 |
| activation (Act-2) | 36674_at | 12.8 | 7.1 | 12 | −1.1 |
| pM5 | 33414_at | 12.8 | 10.2 | 8.8 | 8.2 |
| CCAAT transcription binding factor subunit gamma | 40466_at | 12.8 | 18.3 | 16.7 | 14.6 |
| CD4-related protein involved in lymphocyte activation | 36776_at | 12.8 | 23.0 | 27.0 | 5.0 |
| SYT interacting protein SIP | 41460_at | 12.7 | 10.7 | 10.3 | 15.7 |
| MHC class I | 34934_at | 12.6 | 13.9 | 18.2 | 21.2 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| DNA dependent ATPase and helicase (ATRX) | 818_s_at | 12.6 | 7.4 | 13.3 | 10.0 |
| Brutons tyrosine kinase (BTK), alpha-D-galactosidase A (GLA), L44-like ribosomal protein (L44L) and FTP3 (FTP3) | 36833_at | 12.6 | 6.8 | 4 | 3.9 |
| natural killer cell BY55 | 33112_at | 12.6 | 15.9 | 10 | −2.2 |
| leukocyte IgG receptor (Fc-gamma-R) | 37200_at | 12.5 | 9.8 | 9.7 | −2 |
| KIAA0080 gene | 36144_at | 12.4 | 14.3 | 11.8 | 3.0 |
| tax1-binding protein TXBP181 | 499_at | 12.4 | 11.1 | 17.0 | 6.6 |
| gb = AI652660 | 41590_at | 12.3 | 6.3 | 9.7 | 11.3 |
| C-terminal binding protein 2 | 40780_at | 12.1 | 10.7 | 5.5 | 1.1 |
| NuMA | 33822_at | 11.9 | 11.3 | 19.8 | 25.0 |
| | 160043_at | 11.9 | 6.7 | 3.1 | 4.2 |
| lymphoma proprotein convertase (LPC) | 34361_at | 11.7 | 11.4 | 11.7 | 11.1 |
| RGP3 | 37637_at | 11.4 | 12 | 9.9 | 3 |
| gb = W26655 | 39045_at | 11.3 | 5.6 | 11.7 | 6.2 |
| KIAA0226 gene | 31802_at | 11.3 | 12.4 | 3.8 | 17 |
| KIAA0064 gene | 37654_at | 11.2 | 15.8 | 11.3 | 9.9 |
| G9a | 36200_at | 11.1 | 9.1 | 11.0 | 6.7 |
| Human transforming growth factor-beta type III receptor (TGF-beta) | 1897_at | 11.1 | 7.6 | 9 | 4.3 |
| guanylate binding protein isoform I (GBP-2) | 35735_at | 11.1 | 23.8 | 29.5 | 6 |
| KIAA0199 gene | 37656_at | 11.0 | 10.4 | 14.6 | 15.0 |
| gb = AA194159 | 41282_s_at | 10.9 | 11.3 | 10.7 | 17.7 |
| carnitine palmitoyltransferase I type II | 35936_g_at | 10.9 | 9.1 | 11.8 | 8.8 |
| carnitine palmitoyltransferase I type I | 35228_at | 10.8 | 11.1 | 14.3 | 7.9 |
| Daxx | 41161_at | 10.8 | 10.7 | 15.4 | 13.7 |
| B-ATF | 39942_at | 10.7 | 12 | 10.4 | 2.4 |
| AUH | 37616_at | 10.7 | 8.6 | 16.0 | 10.5 |
| (TAFII70-alpha) | 37271_at | 10.7 | 6.9 | 8.6 | 11.1 |
| serine protease-like protein | 37137_at | 10.6 | 5.8 | 6.2 | 1.2 |
| T-cell receptor Ti rearranged gamma-chain mRNA V-J-C region | 41468_at | 10.6 | 19 | 25.1 | 9.7 |
| PEST phosphatase interacting protein homolog (H-PIP) | 34914_at | 10.6 | 8.1 | 8.3 | 8.2 |
| KIAA0808 protein | 33316_at | 10.3 | 4.8 | 5.6 | 1.5 |
| nuclear protein, NP220 | 32674_at | 10.3 | 7.5 | 12.1 | 15.3 |
| beta-galactoside alpha-2,6-slalyltransferase | 41352_at | 10.2 | 8.9 | 6.1 | 13.8 |
| HREV107-like protein | 35704_at | 10 | 8.9 | 5.4 | −1.6 |
| adenylyl cyclase type IX | 33800_at | 9.9 | 8.4 | 8.1 | 4.3 |
| guanine nucleotide exchange factor mss4 | 38264_at | 9.9 | 9.3 | 11.4 | 12.9 |
| fibrinogen-like protein (pT49 protein) | 39591_s_at | 9.9 | 14 | 12.1 | −3.1 |
| XAP-5 | 38599_s_at | 9.8 | 9.5 | 12.2 | 10.1 |
| DNA from chromosome 19p13.2 cosmids R31240, R30272 and R28549 containing the EKLF, GCDH, CRTC, and RAD23A genes | 1750_at | 9.7 | 10.4 | 12.0 | 14.8 |
| guanine nucleotide exchange factor | 33260_at | 9.6 | 6.9 | 6.2 | 4.7 |
| DEAD-box protein p72 (P72) | 41260_at | 9.4 | 14.0 | 87.2 | 23.5 |
| calcium/calmodulin-dependent protein kinase II | 32105_f_at | 9.4 | 7.3 | 10.3 | 7.2 |
| IFN-gamma | 40702_at | 9.3 | 11.7 | 9.4 | −2.8 |
| IL-17 | 36229_at | 9.3 | 19.1 | 4.6 | 25.5 |
| KIAA0122 gene | 40070_at | 9.3 | 4.1 | 10.4 | 5 |
| NKG2D gene, exons 2–5 | 36777_at | 9.3 | 8.7 | 8 | 12.6 |
| alanyl-tRNA synthetase | 36185_at | 9.2 | 12.1 | 15.8 | 25.5 |
| gb = AL080203 | 40451_at | 9.1 | 13.2 | 10.2 | 11.5 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| gb = AA524058 | 34359_at | 9 | 6.1 | 4.6 | 7.6 |
| P-glycoprotein (PGY1) | 1576_g_at | 9.0 | 8.6 | 18.1 | 14.9 |
| bcl-xL | 34742_at | 8.9 | 6.6 | 3.4 | 7.3 |
| putative dienoyl-CoA isomerase (ECH1) gene | 32756_at | 8.9 | 12 | 11.8 | 10.9 |
| KIAA0248 gene | 40123_at | 8.9 | 5.4 | 4.8 | 4.3 |
| gb = AF070533 | 41744_at | 8.8 | 7.8 | 7.7 | 8.7 |
| alpha-2,3-sialyltransferase (SIAT4A) | 40290_f_at | 8.8 | 7.7 | 10.2 | 10.2 |
| ADP-ribosylation factor | 36193_at | 8.8 | 9.1 | 9.1 | 11.7 |
| gb = AI540958 | 34891_at | 8.8 | 12.6 | 10.1 | 8.4 |
| oligo A synthetase E | 38388_at | 8.8 | 7.8 | 16.8 | 1.2 |
| gb = AA631972 | 39119_s_at | 8.7 | 9.8 | 7.1 | 4.5 |
| pyruvate dehydrogenase (EC 1.2.4.1) beta subunit | 39160_at | 8.7 | 4 | 6.2 | 6.2 |
| gb = AI432401 | 39593_at | 8.7 | 19.3 | 20.2 | −6.9 |
| gb = U51712 | 39698_at | 8.6 | 9.6 | 3.3 | 3.9 |
| glucocerebrosidase (GCB) | 32632_g_at | 8.6 | 10.3 | 8.3 | 7.5 |
| T cell-specific protein (RANTES) | 1405_1_at | 8.6 | 8.1 | 9.4 | 4.9 |
| aminoacylase-1 (ACY1) | 37713_at | 8.6 | 9.0 | 5.6 | 9.7 |
| multidrug resistance protein 5 (MRP5) | 1933_g_at | 8.4 | 9.4 | 5.4 | 3.4 |
| gb = AL050259 | 40521_at | 8.2 | 7.3 | 10.7 | 7.5 |
| carboxyl methyltransferase | 37736_at | 8.2 | 9.6 | 6.4 | 10.1 |
| gb = AA176780 | 40485_at | 8.2 | 15.9 | 10.2 | 21.7 |
| KIAA0955 protein | 41100_at | 8.2 | 8.1 | 11.1 | 10.8 |
| gb = AL079277 | 41710_at | 8.1 | 7.7 | 3.1 | −1.7 |
| KIAA0129 gene | 33253_at | 8.1 | 11.1 | 7.4 | 10.6 |
| gb = AA156987 | 39162_at | 8.0 | 11.1 | 7.3 | 14.8 |
| testis-specific cAMP-dependent protein kinase catalytic subunit (C-beta isoform) | 36215_at | 7.9 | 5.1 | 5.9 | 7.3 |
| KIAA0898 protein | 33107_at | 7.8 | 4.5 | 7.9 | 8.1 |
| tactile protein | 34961_at | 7.8 | 8.5 | 5.4 | 28.1 |
| 3-alkyladenine DNA glycosylase (HAAG) | 37768_at | 7.8 | 6.3 | 8.7 | 9.8 |
| helicase-like protein (HLP) | 37998_at | 7.8 | 9.0 | 9.2 | 11.8 |
| 17-beta-hydroxysteroid dehydrogenase | 36626_at | 7.8 | 8.8 | 38.2 | 7.9 |
| gb = AF035282 | 41679_at | 7.7 | 5.7 | 6.8 | 3.8 |
| beta2-chimaerin | 33244_at | 7.6 | 7.2 | 4.6 | −1.5 |
| butyrophilin (BTF3) | 38241_at | 7.6 | 6.2 | 8.8 | 4.2 |
| protein kinase C-theta (PRKCT) | 38949_at | 7.6 | 5.1 | 8.8 | 7.5 |
| homolog of yeast mutL (hPMS1) gene | 525_g_at | 7.5 | 6.9 | 9.0 | 9.1 |
| heat shock protein (hsp 70) | 1104_s_at | 7.5 | 19.3 | 13.1 | 8.4 |
| receptor protein 4-1BB | 31540_at | 7.5 | 7.4 | 8.7 | −1.2 |
| fibrinogen-like protein (pT49 protein) | 39592_r_at | 7.4 | 8.4 | 7.0 | −1.6 |
| RLIP76 | 36626_at | 7.4 | 8.2 | 8.6 | 11.6 |
| copper chaperone for superoxide dismutase (CCS) | 36068_at | 7.3 | 7.8 | 10.5 | 9.3 |
| TAR RNA binding protein 2 (TRBP2) | 35657_at | 7.3 | 7.3 | 5.5 | 7.3 |
| N-myristoyltransferase 1 | 39000_at | 7.3 | 10.0 | 10.0 | 13.8 |
| gb = AA126515 | 41172_at | 7.3 | 5.4 | 8.8 | 8.9 |
| gb = W27519 | 32326_at | 7.3 | 5 | 6.9 | 9.1 |
| synaptogyrin 3 | 40314_at | 7.2 | 7.4 | 9.7 | 3.4 |
| gb = AI862521 | 39743_at | 7.2 | 4.7 | 4.7 | 5.5 |
| Human replication protein A | 1382_at | 7.2 | 4.0 | 4.8 | 6.9 |
| puromycin sensitive aminopeptidase | 39431_at | 7.2 | 5.2 | 15.4 | 9.9 |
| gb = AI014538 | 38623_at | 7.2 | 7.9 | 7.2 | 9.9 |
| gb = AF055004 | 34831_at | 7.2 | 6.5 | 6.9 | 3.6 |
| Endothelial Cell Growth Factor 1 | 1665_s_at | 7.2 | 28.7 | 32.9 | −11.3 |
| gb = AL040137 | 41807_at | 7.2 | 7.3 | 8.7 | 4.1 |
| gb = AF007155 | 40472_at | 7.1 | 6.6 | 6.9 | 6.7 |
| lymphoid phosphatase LyP1 | 36808_at | 7.1 | 3.1 | 5.6 | 2.7 |
| Hanukah factor serine protease (HuHF) | 40757_at | 7.1 | 6.1 | 4.6 | 1.3 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| TM7XN1 | 35789_at | 7.1 | 5 | 5.4 | 1.1 |
| gb = AB011133 | 33223_at | 7 | 6.1 | 4.9 | 2 |
| cyclin-dependent kinase 4 (CDK4) | 1942_s_at | 7.0 | 7.5 | 5.4 | 10.2 |
| WD repeat protein HAN11 | 38171_at | 7.0 | 4.0 | 3.5 | 2.7 |
| T cell-specific protein (RANTES) | 1403_s_at | 7 | 5.7 | 6.8 | 3.4 |
| KIAA0067 gene | 34189_at | 7.0 | 7.9 | 11.8 | 10.4 |
| gb = AI670100 | 34724_at | 7.0 | 7.9 | 6.5 | 5.2 |
| BRCA1, Rho7 and vat1 genes, complete cds, and ipf35 gene | 626_s_at | 6.9 | 13.4 | 8.2 | 1.9 |
| gb = H68340 | 41446_f_at | 6.9 | 7.2 | 13 | 3.3 |
| RasGAP-related protein (IQGAP2) | 37276_at | 6.9 | 4 | 8.1 | 2.7 |
| RBP2-retinoblastoma binding protein 2 | 36999_at | 6.9 | 8.5 | 13.3 | 15.9 |
| KIAA0102 gene | 37359_at | 6.8 | 5.8 | 3.7 | 4.8 |
| gb = AL050060 | 35840_at | 6.8 | 17 | 5.9 | 4.5 |
| clk2 | 646_s_at | 6.8 | 9.5 | 11.5 | 13.8 |
| gb = AL048308 | 32768_at | 6.7 | 5.3 | 7.1 | 5.2 |
| gb = AA877795 | 33854_at | 6.7 | 7.3 | 9.2 | 5.7 |
| KIAA1062 protein | 38313_at | 6.7 | 3.1 | 3.5 | 1.1 |
| a-glucosidase I | 38464_at | 6.7 | 6 | 6.9 | 9.9 |
| retinoblastoma | 40418_at | 6.7 | 6.8 | 5.1 | 5.2 |
| gb = AF026402 | 40465_at | 6.7 | 8.2 | 8.9 | 8.3 |
| metase (MET-1) | 32264_at | 6.7 | 4.4 | 3.1 | 1.2 |
| axin (AXIN) | 33319_at | 6.6 | 6.3 | 4 | 4.2 |
| adenylate kinase (AK1) | 36997_at | 6.6 | 4.8 | 10.9 | 5.7 |
| cbl-b | 514_at | 6.6 | 5.4 | 11.4 | 13.6 |
| T-cell differentiation antigen Leu-2/T8 | 40699_at | 6.6 | 5.6 | 4.8 | 4.1 |
| gb = W28892 | 33850_at | 6.5 | 7.8 | 6.5 | 8.9 |
| m6A methyltransferase (MT-A70) | 32246_g_at | 6.5 | 6.7 | 8.5 | 13 |
| 1,4-alpha-glucan branching enzyme (HGBE) | 32643_at | 6.5 | 6.1 | 7.1 | 9.3 |
| DP prostanoid receptor (PTGDR) | 31782_at | 6.4 | 6.7 | 3.6 | 4.3 |
| interleukin 2 receptor gamma chain | 1506_at | 6.4 | 4.2 | 4.1 | 4.1 |
| translational inhibitor protein | 32173_at | 6.4 | 5.5 | 4.5 | 4.9 |
| gb = AI800578 | 34728_g_at | 6.4 | 7.7 | 9.2 | 8.1 |
| tudor repeat associator with PCTAIRE 2 | 40852_at | 6.4 | 7.0 | 7.7 | 6.8 |
| gb = AL080111 | 34752_at | 6.3 | 3.9 | 7.9 | 7.4 |
| granulocyte colony-stimulating factor induced gene | 37121_at | 6.3 | 4.9 | 4.7 | 1.1 |
| carboxyl terminal LIM domain protein (CLIM1) | 36937_s_at | 6.3 | 6.1 | 4.4 | −1.6 |
| gb = AF091084 | 35329_at | 6.3 | 9.1 | 6.9 | 11.4 |
| gb = AL041663 | 32662_at | 6.3 | 4.7 | 4.3 | 5.2 |
| gb = AAI60056 | 40937_at | 6.3 | 4.8 | 5.0 | 12.5 |
| NK receptor (NKp46), isoform d | 34040_s_at | 6.3 | 6.3 | 7.4 | 3.6 |
| serine/threonine protein kinase EMK | 965_at | 6.3 | 6.9 | 6.1 | 8.7 |
| small GTP-binding protein | 40669_at | 6.3 | 5.1 | 5.4 | 2.3 |
| gb = AA576724 | 41646_at | 6.3 | 5.8 | 6.4 | 5.6 |
| RING zinc finger protein (RZF) | 35811_at | 6.3 | 6 | 8.5 | 4.7 |
| KIAA0010 gene | 32044_at | 6.2 | 7.1 | 6.3 | 7.2 |
| TBP-associated factor (hTAFII130) | 142_at | 6.2 | 5.7 | 5.8 | 6.8 |
| gb = AW024285 | 41177_at | 6.2 | 6.3 | 3.7 | 2.6 |
| gb = D50920 | 34289_f_at | 6.2 | 6.2 | 4.4 | 7.6 |
| GARS-AIRS-GART | 38384_at | 6.2 | 7.3 | 8.6 | 7.5 |
| SCA2 | 36998_s_at | 6.2 | 6 | 7.4 | 9.5 |
| sigma 3B | 32030_at | 6.1 | 4.6 | 6.7 | 1.5 |
| KIAA0386 gene | 37112_at | 6.1 | 6.3 | 4.1 | 18.1 |
| nucleolar protein hNop56 | 34882_at | 6.1 | 5.5 | 4.2 | 11.4 |
| RP105 | 40715_at | 6.0 | 10.1 | 6.0 | 5.2 |
| gb = W28167 | 34404_at | 6.0 | 6.3 | 5.4 | 7.9 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| MAP kinase kinase 4 (MKK4) | 36910_at | 6.0 | 4.4 | 7.4 | 7.5 |
| eIF4GII | 33907_at | 5.9 | 5.9 | 7.5 | 2.6 |
| WWp2-like mRNA | 33629_at | 5.9 | 6.1 | 5.3 | 2.9 |
| G6PD gene for glucose-6-phosphate dehydrogenase | 38043_at | 5.9 | 3.5 | 4.8 | 9.0 |
| LTG19 | 32400_at | 5.9 | 6.2 | 6.3 | 5.4 |
| KIAA0796 protein | 38113_at | 5.9 | 4.2 | 5.3 | 3.2 |
| interleukin 2 receptor beta chain (p70–75) | 1365_at | 5.9 | 5 | 4.8 | 1.1 |
| KIAA0060 gene | 34332_at | 5.8 | 7.8 | 7.9 | 14.5 |
| low density lipoprotein receptor gene | 32855_at | 5.8 | 10.1 | 5.2 | 28.0 |
| Huntingtons Disease (HD) | 37767_at | 5.8 | 4.7 | 4.7 | 3.8 |
| monocarboxylate transporter 2 (hMCT2) | 35547_at | 5.8 | 5.1 | 6 | 14.1 |
| DNA from chromosome 19p13.2 cosmids R31240, R30272 and R28549 containing the EKLF, GCDH, CRTC, and RAD23A genes | 1753_s_at | 5.8 | 3.1 | 8.3 | 4.6 |
| KIAA0053 gene | 38149_at | 5.8 | 5.2 | 9 | 5 |
| Gb = AI143868 | 34816_at | 5.8 | 4.6 | 5.1 | 7.7 |
| serine phosphatase FCP1a (FCP1) | 35979_at | 5.8 | 6.2 | 5.4 | 5.2 |
| similar to cytoplasmic dynein light chain 1 | 31655_at | 5.7 | 7.7 | 6.9 | 3.2 |
| KIAA1064 protein | 36860_at | 5.7 | 5.2 | 3.1 | 5.9 |
| transactivator protein (CREB) | 37535_at | 5.7 | 5.8 | 8.6 | 10.2 |
| Human immune interferon (IFN-gamma) | 1611_s_at | 5.7 | 5.3 | 4.5 | −1 |
| gb = AF052135 | 39391_at | 5.7 | 8 | 7.6 | 9.7 |
| acylphosphatase, erythrocyte (CT) isoenzyme | 33334_at | 5.6 | 4.9 | 5.5 | 7.5 |
| hRIf beta subunit (p102 protein) | 33252_at | 5.6 | 6.0 | 4.2 | 5.2 |
| ABC transporter MOAT-C (MOAT-C) | 41428_at | 5.6 | 6.9 | 8.3 | 9.1 |
| ras GTPase-activating-like protein (IQGAP1) | 1825_at | 5.6 | 6.2 | 6.1 | 4.2 |
| protein tyrosine phosphatase (PTPase-alpha) | 1496_at | 5.6 | 3.8 | 5.2 | 3 |
| retinoblastoma susceptibility | 2044_s_at | 5.6 | 4.4 | 5.5 | 2.3 |
| KIAA0877 protein | 39021_at | 5.6 | 5.3 | 4.5 | 4.5 |
| translocation T(4:11) of ALL-1 gene to chromosome 4 | 1124_at | 5.5 | 4 | 7.6 | 6.4 |
| osteoclast stimulating factor mRNA | 467_at | 5.5 | 4.9 | 4.4 | 4.1 |
| kinesin-like DNA binding protein | 356_at | 5.5 | 5.1 | 9.2 | 6.5 |
| IkB kinase beta subunit | 35960_at | 5.5 | 4.1 | 5.4 | 3.9 |
| gb = AW044624 | 41551_at | 5.4 | 5 | 6.6 | 4.6 |
| gb = AA127624 | 33865_at | 5.4 | 3.8 | 4.6 | 6.5 |
| RNA binding protein DEF-3 | 40869_at | 5.4 | 6.0 | 6.8 | 6.7 |
| protein phosphatase 2A B alpha1 regulatory subunit | 176_at | 5.4 | 4.4 | 7.8 | 6.1 |
| ntegrin beta-7 subunit | 2019_s_at | 5.4 | 5.9 | 3.8 | 5.3 |
| cdc25+ homolog | 1347_at | 5.4 | 4.7 | 3.8 | 10.3 |
| Ndr protein kinase | 36217_at | 5.3 | 4.3 | 7.7 | 7.2 |
| KIAA0625 protein | 40083_at | 5.3 | 6.6 | 7.9 | 8 |
| KIAA1012 protein | 36002_at | 5.3 | 6.5 | 8 | 8.3 |
| protein phosphatase 2A Balpha1 regulatory subunit | 40786_at | 5.3 | 4.2 | 7.2 | 6.3 |
| WD40 protein BING4 | 33250_at | 5.3 | 4.0 | 3.4 | 5.5 |
| serine kinase SRPK2 | 1213_at | 5.3 | 3.3 | 7.7 | 2.2 |
| interferon regulatory factor 3 | 371_at | 5.3 | 4.3 | 5.7 | 5.9 |
| nuclear localization signal containing protein deleted in Velo-Cardio-Facial syndrome (NIvcf) | 32745_at | 5.2 | 4.9 | 4.4 | 4.4 |
| gb = D45288 | 35310_at | 5.2 | 3.2 | 3.3 | 2.1 |
| gb = AI698103 | 35993_s_at | 5.2 | 7.4 | 6.3 | 8.6 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| gb = X95808 | 41046_s_at | 5.2 | 5.7 | 8.3 | 11.3 |
| endo/exonuclease Mre11 (MRE11A) | 32870_g_at | 5.2 | 4.3 | 5.9 | 6.3 |
| beige protein homolog (chs) | 35695_at | 5.2 | 5 | 7.6 | 2.9 |
| gb = AL049703 | 32212_at | 5.1 | 5.2 | 4.0 | 6.4 |
| leucocyte vacuolar protein sorting | 35779_at | 5.1 | 8.4 | 6.3 | 6 |
| programmed cell death-2/Rp8 homolog | 855_at | 5.1 | 7.3 | 4.3 | 7.8 |
| malate dehydrogenase precursor (MDH) mRNA, nuclear gene encoding mitochondrial protein | 39001_at | 5.0 | 4.5 | 4.6 | 5.2 |
| gb = AL049955 | 34347_at | 5 | 3.3 | 5.5 | 7 |
| gb = U37012 | 33132_at | 5 | 16.8 | 3.4 | 7.2 |
| gb = D82351 | 31671_at | 5 | 3.9 | 4.2 | 3.2 |
| uracil-DNA glycosylase | 37686_s_at | 5.0 | 3.5 | 5.9 | 5.5 |
| KIAA0011 gene | 36932_at | 5.0 | 4.5 | 5.8 | 7.8 |
| YL-1 protein (nuclear protein with DNA-binding ability) | 33873_at | 5 | 4.2 | 6.7 | 7.1 |
| tRNA synthetase-like protein | 34291_at | 5 | 7 | 6 | 8.2 |
| protein kinase C-binding protein RACK7 | 842_at | 5.0 | 4.9 | 3.8 | 4.6 |
| KIAA0312 gene | 34372_at | 5.0 | 3.7 | 6.7 | 4.7 |
| SF2p33 | 36099_at | 4.9 | 4.6 | 3.7 | 5.0 |
| gb = AB014597 | 39380_at | 4.9 | 3.5 | 3.7 | 4.3 |
| gb = R59697 | 35140_at | 4.9 | 4.1 | 4.6 | 6.4 |
| gb = U36501 | 37354_at | 4.9 | 5.2 | 3.4 | 5.4 |
| ZBP-59 protein | 41465_at | 4.9 | 3.6 | 5.2 | 5.1 |
| ribulose-5-phosphate-epimerase | 37797_at | 4.9 | 4.0 | 7.2 | 9.2 |
| C2f | 39357_at | 4.9 | 5.1 | 4.9 | 6.6 |
| GT335 | 41749_at | 4.9 | 5 | 5.9 | 4.3 |
| Human poly(ADP-ribose) synthetase | 1287_at | 4.9 | 6 | 4.4 | 7.5 |
| KIAA0132 gene | 35322_at | 4.9 | 6.3 | 9.3 | 6.2 |
| gb = AF052162 | 41176_at | 4.8 | 4.4 | 3.4 | 1.7 |
| class I histocompatibility antigen-like protein mRNA | 34427_g_at | 4.8 | 3.1 | 4.0 | 4.0 |
| gb = AF060862 | 40352_at | 4.8 | 3.9 | 3.3 | 2.6 |
| G4 protein (G4 gene, located in the class III region of the major histocompatiblity complex | 41053_at | 4.8 | 6.1 | 4.7 | 8.2 |
| putative mitochondrial outer membrane protein import receptor (hTOM) | 34345_at | 4.8 | 6.4 | 4.4 | 7.2 |
| nitrilase1 (NIT1) | 39735_at | 4.8 | 3.8 | 7.6 | 7.1 |
| gb = L13435 | 160024_at | 4.8 | 5.7 | 3.1 | 6.7 |
| gb = L13435 | 33126_at | 4.8 | 4.1 | 6.5 | 5.6 |
| Smg GDS-associated protein SMAP | 40779_at | 4.8 | 3.9 | 4.4 | 6.3 |
| KIAA0854 protein | 41503_at | 4.7 | 3.4 | 4.3 | 4.2 |
| gb = AA173896 | 34340_at | 4.7 | 9.3 | 6.5 | 8 |
| gb = AA975427 | 31736_at | 4.7 | 4.1 | 4.1 | 4 |
| gb = W27939 | 38656_s_at | 4.7 | 3.6 | 3.9 | 4.3 |
| Human translational initiation factor (eIF-2) | 1154_at | 4.7 | 5.3 | 4 | 2.9 |
| NADP-dependent isocitrate dehydrogenase (IDH) | 39023_at | 4.7 | 8.9 | 12.6 | 5.8 |
| heterochromatin protein p25 | 37304_at | 4.7 | 4.6 | 5.7 | 5.7 |
| mRNA for small GTP-binding protein | 37466_at | 4.7 | 6.4 | 5.4 | 6.3 |
| methyl-CpG-binding protein | 34355_at | 4.7 | 4.4 | 4.6 | 5.6 |
| mRNA for imogen | 40072_at | 4.6 | 4.2 | 4.9 | 6.6 |
| transcription factor NFATx4 | 40823_s_at | 4.6 | 4.5 | 3.1 | 3.9 |
| nexin 1 (SNX1) | 36583_at | 4.6 | 8.5 | 12.3 | 9.8 |
| gb = U79282 | 32059_at | 4.6 | 4.0 | 5.2 | 4.2 |
| gb = AI760162 | 41058_g_at | 4.6 | 7.3 | 6.0 | 8.6 |
| gb = AA224832 | 39120_at | 4.6 | 5.7 | 9.3 | 9.4 |
| KIAA0648 protein | 34353_at | 4.6 | 3.1 | 5.1 | 6.4 |
| gb = AB007889 | 37363_at | 4.6 | 4 | 5.5 | 1.3 |
| homolog of yeast mutL (hPMS1) | 41461_at | 4.6 | 3.6 | 4.5 | 5.5 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| UDP-glucose dehydrogenase (UGDH) | 35214_at | 4.6 | 3.9 | 4 | 6.4 |
| KIAA0560 protein | 41712_at | 4.5 | 4.2 | 5.3 | 6.8 |
| gb = AL050390 | 31852_at | 4.5 | 3.8 | 3.7 | 3.6 |
| similar to Drosophila ash2 | 35804_at | 4.5 | 5.8 | 6.5 | 5.7 |
| gb = AI928387 | 33225_at | 4.5 | 4.5 | 4.6 | 5.4 |
| SCM-1beta precursor | 31496_g_at | 4.5 | 25.9 | 8.2 | 5.7 |
| putative glucosyltransferase | 32051_at | 4.5 | 4.6 | 3 | 5.7 |
| retinoic acid receptor responder 3 (RARRES3) | 33236_at | 4.5 | 4.2 | 4.6 | 1.6 |
| KIAA0350 gene | 34661_at | 4.5 | 5.4 | 3 | 5.1 |
| CACCC box-binding protein | 41466_s_at | 4.5 | 3.1 | 4.3 | 3.9 |
| mutator gene (hMSH2) | 860_at | 4.5 | 5.0 | 3.8 | 13.1 |
| tyrosylprotein sulfotransferase-2 | 35172_at | 4.5 | 5 | 4.2 | 3 |
| DNA polymerase gamma | 1014_at | 4.4 | 3.5 | 4.6 | 4 |
| DORA protein | 34946_at | 4.4 | 14.8 | 13.2 | −3.0 |
| gb = AI246726 | 37046_at | 4.4 | 4.3 | 3.8 | 5.9 |
| galactokinase (GK2) | 37825_at | 4.4 | 3.7 | 4.7 | 3.4 |
| gb = AW051579 | 33191_at | 4.4 | 4.2 | 3.6 | 4.5 |
| Heat shock protein 70 testis variant | 40656_at | 4.4 | 5.0 | 4.1 | 5.9 |
| gb = AA142942 | 33399_at | 4.4 | 5.3 | 4.3 | 4.6 |
| gb = U26710 | 35632_at | 4.4 | 3.1 | 5.4 | 7.4 |
| stress-activated protein kinase 4 | 33245_at | 4.4 | 3.8 | 4.0 | 3.3 |
| ST15 | 35234_at | 4.3 | 3.3 | 3.9 | 6.2 |
| villin-like protein | 37123_at | 4.3 | 3.4 | 4.1 | 3.6 |
| gb = U79256 | 37577_at | 4.3 | 3.2 | 4.7 | 2.5 |
| gb = L13744 | 35975_at | 4.3 | 3.4 | 5.9 | 8.3 |
| gb = AL049701 | 34446_at | 4.3 | 3.3 | 5.1 | 2 |
| FIP2 alternatively translated | 41743_i_at | 4.3 | 4.3 | 4.9 | 4.3 |
| NF-AT4c | 40822_at | 4.3 | 4.1 | 4.5 | 3.9 |
| putative poly(ADP-ribosyl) transferase (PARPL) | 37303_at | 4.3 | 4.4 | 4.9 | 4.6 |
| KIAA0373 gene | 38135_at | 4.3 | 3.8 | 5.4 | 5.8 |
| gb = W26640 | 35357_at | 4.3 | 4 | 3.4 | 9.3 |
| SCM-1beta precursor | 31495_at | 4.2 | 31.5 | 8.8 | 8.1 |
| gb = D87077 | 38892_at | 4.2 | 3.9 | 5.1 | 4.1 |
| mitochondrial RNA polymerase | 40232_at | 4.2 | 3.5 | 5.3 | 4.7 |
| gb = AA780049 | 40615_at | 4.2 | 4.1 | 5.4 | 3.2 |
| gb = AA905543 | 38620_at | 4.2 | 5.0 | 4.6 | 2.7 |
| (AF1q) | 36941_at | 4.2 | 4.0 | 5.1 | 11.1 |
| KIAA0018 gene | 36658_at | 4.2 | 5.9 | 3.1 | 4.7 |
| platelet activating receptor homolog (H963) | 31919_at | 4.2 | 3.4 | 13.9 | 9.9 |
| SET-binding protein (SEB) | 34990_at | 4.2 | 4.3 | 6.2 | 1.3 |
| transformation sensitive protein (IEF SSP 3521) | 207_at | 4.2 | 8.3 | 3.6 | 6.6 |
| protein-tyrosine phosphatase | 1460_g_at | 4.2 | 4.2 | 6.4 | 4.1 |
| (GalT3 (beta3-Galactosyltransferase)) | 35944_at | 4.1 | 3.9 | 5.4 | 3.5 |
| Arp2/3 protein complex subunit p16-Arc (Arc16) | 38392_at | 4.1 | 3.8 | 3.7 | 3.9 |
| nuclear receptor co-repessor N-CoR | 39722_at | 4.1 | 5.1 | 6.1 | 4.2 |
| gb = AA808961 | 38287_at | 4.1 | 5.2 | 4.4 | 2.3 |
| transcription factor ISGF-3 | AFFX-HUMISGF3A/M97935_3_at | 4.1 | 5.2 | 7.3 | 2.7 |
| Jak2 kinase | 37468_at | 4.1 | 5.1 | 5.5 | 3.5 |
| transcription factor ISGF-3 | AFFX-HUMISGF3A/M97935_MA_at | 4.1 | 3.9 | 6.9 | 1 |
| p21-activated protein kinase (Pak1) | 1558_g_at | 4.1 | 6.9 | 5.1 | −1.5 |
| gb = D79985 | 33889_s_at | 4.1 | 3.8 | 4.6 | 7.1 |
| gb = AB002347 | 39797_at | 4.1 | 4.5 | 7.1 | 8.1 |
| gb = D79998 | 34858_at | 4.1 | 3.8 | 4.7 | 8.8 |
| short form transcription factor C-MAF (c-maf) | 41505_r_at | 4.1 | 4.8 | 3.1 | 2.6 |
| gb = AW051579 | 33192_g_at | 4.1 | 5.2 | 5.7 | 5.8 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| lycosylphosphatidyl inositol-anchored protein GPI-80 | 34498_at | 4.1 | 3.7 | 11.2 | 1.6 |
| DNA helicase (RECQL) | 34684_at | 4.1 | 5.2 | 7 | 8.6 |
| KIAA0838 protein | 34719_at | 4.1 | 4 | 6.2 | 7.4 |
| SKAP55 | 38862_at | 4.1 | 3.3 | 4.3 | 2.2 |
| Sel-1 like mRNA | 40689_at | 4 | 3.4 | 3.6 | 3.4 |
| c-myc binding protein | 1904_at | 4 | 5.3 | 3.4 | 4.1 |
| T-cell receptor alpha chain C region | 432_s_at | 4 | 5.1 | 3 | 4.8 |
| calcium activated neutral protease large subunit (muCANP, calpain, EC 3.4.22.17) | 33908_at | 4 | 5.5 | 3.9 | 3.5 |
| uridine diphosphoglucose pyrophosphorylase | 37373_at | 4 | 3.6 | 3.7 | 3.7 |
| SH2D1A | 38147_at | 4 | 3.4 | 4.4 | 3.9 |
| gb = AL035296 | 37119_at | 4.0 | 3.4 | 6.4 | 5.3 |
| gb = AF070595 | 38170_at | 4.0 | 3.0 | 4.2 | 6.5 |
| gb = H05692 | 35283_at | 3.9 | 4.0 | 5.4 | 5.4 |
| gb = AI540318 | 41234_at | 3.9 | 3.5 | 5.5 | 3.4 |
| gb = X79882 | 38064_at | 3.9 | 4.7 | 3.3 | 2.3 |
| GAP binding protein p62dok (DOK) | 815_at | 3.9 | 5.3 | 6.9 | 3.7 |
| OPA-containing protein | 40998_at | 3.9 | 4 | 4.1 | 5.4 |
| myogenic determining factor 3 (MYOD1) | 33482_at | 3.9 | 4.0 | 4.2 | 4.9 |
| gb = AA203354 | 38981_at | 3.9 | 6.2 | 3.7 | 5.7 |
| gb = AF006083 | 35271_at | 3.9 | 3.4 | 3.1 | 3.2 |
| ICAM-2 | 38454_g_at | 3.9 | 6.4 | 3 | 5.7 |
| protein-tyrosine phosphatase | 1459_at | 3.9 | 3.2 | 5.9 | 3.7 |
| T-lymphocyte specific protein tyrosine kinase p56lck (lck) abberant mRNA | 33238_at | 3.9 | 3.6 | 3.7 | 4.7 |
| zinc finger protein | 39261_at | 3.9 | 4.0 | 6.7 | 7.4 |
| KIAA0097 gene | 37293_at | 3.8 | 3.4 | 5.4 | 4.3 |
| cytosalic acetoacatyl-coenzyme A thiolase | 34790_at | 3.8 | 3.1 | 3.2 | 6.8 |
| NF-AT4c | 250_at | 3.8 | 3 | 4 | 2.7 |
| gb = X77744 | 32883_at | 3.8 | 4 | 6.1 | 5.4 |
| gb = Y08614 | 37729_at | 3.8 | 3.9 | 4.5 | 3.8 |
| transcription factor WSTF | 32261_at | 3.8 | 4.4 | 5 | 5.5 |
| TATA-binding protein mRNA | 41441_at | 3.8 | 3.2 | 4.6 | 7.3 |
| KIAA0543 protein | 41077_at | 3.8 | 4.6 | 5.5 | 12.7 |
| lymphocyte-specific protein tyrosine kinase (lck) | 2059_s_at | 3.7 | 3.9 | 4.1 | 4.7 |
| CHD5 protein | 32777_at | 3.7 | 3.3 | 6.7 | 5.4 |
| KIAA0549 | 40064_at | 3.7 | 4 | 3.3 | 4.9 |
| leukemia associated gene 1 | 33791_at | 3.7 | 5.4 | 3.1 | 3.9 |
| Diff33 | 37007_at | 3.7 | 3.9 | 4.6 | 5.6 |
| branched chain alpha-ketoacid dehydrogenasekinase precursor | 32828_at | 3.7 | 3.2 | 7.6 | 2.9 |
| gb = AL022398 | 40720_at | 3.7 | 3.8 | 3.1 | 5.4 |
| KIAA0746 protein | 41585_at | 3.7 | 3.5 | 5.5 | 3.6 |
| gb = AL050018 | 36875_at | 3.7 | 5.2 | 3.2 | 4.8 |
| gb = D25538 | 40585_at | 3.7 | 4.3 | 3.8 | 1.9 |
| gb = X84908 | 37392_at | 3.7 | 3.9 | 5.9 | 2.9 |
| /gb = X70476 | 36677_at | 3.6 | 3.8 | 4.8 | 4.4 |
| interleukin 1-beta converting enzyme isoform beta (IL1BCE) | 39320_at | 3.6 | 6.6 | 3.1 | −1.8 |
| Rad50 | 1533_at | 3.6 | 3.4 | 3.7 | 3.6 |
| snRNA activating protein complex 190 kD subunit (SNAP190) | 35092_at | 3.6 | 6.6 | 3.9 | 6.4 |
| gb = AI655015 | 39932_at | 3.6 | 6.8 | 5 | 6.2 |
| TGF-beta activated kinase 1a | 36905_at | 3.6 | 3.6 | 5.1 | 7 |
| TAFII20 | 802_at | 3.6 | 4.0 | 5.1 | 4.9 |
| gb = AA203246 | 41821_at | 3.6 | 4.1 | 4.8 | 4.2 |
| KIAA0039 gene | 37646_at | 3.6 | 3.0 | 5.1 | 3.2 |
| KIAA0494 | 41830_at | 3.5 | 3.8 | 3.4 | 4.3 |
| gb = AI547262 | 33875_at | 3.5 | 3.1 | 3.3 | 2 |

TABLE 2-continued

Genes upregulated in LGL1, LGL2 and LGL3/RA (Affymetrix U 95)

| Gene Name | Accession No. | LGL1 | LGL2 | LGL3/RA | CD8+ Normal |
|---|---|---|---|---|---|
| | | (Fold increase compared to PBMC) | | | |
| gb = AC002310 | 40905_at | 3.5 | 4.0 | 7.5 | 4.0 |
| MHC class III HSP70-2 gene (HLA) | 31692_at | 3.5 | 8.2 | 5.1 | 4.3 |
| T-cell surface antigen CD2 (T11) | 40738_at | 3.5 | 4.2 | 4.2 | 3.5 |
| tob family | 39286_at | 3.5 | 3.3 | 5.9 | 5.8 |
| phosphoribosypyrophosphate synthetase-associated protein 39 | 37338_at | 3.5 | 4.6 | 4.3 | 6.9 |
| P-selectin glycoprotein ligand (SELPLG) | 37541_at | 3.5 | 3.2 | 3.1 | 3.2 |
| leupaxin | 36062_at | 3.5 | 3.4 | 4.7 | 5.5 |
| KIAA0992 protein | 41191_at | 3.5 | 3.6 | 6.5 | −1.5 |
| gb = W22296 | 36957_at | 3.4 | 3.1 | 3.4 | 3 |
| protoporphyrinogen oxidase | 37098_at | 3.4 | 3.7 | 4.2 | 8.2 |
| prolyl oligopeptidase | 37950_at | 3.4 | 3.6 | 4.7 | 2.4 |
| Toll/interleukin-1 receptor-like protein 3 (TIL3) | 34473_at | 3.4 | 4.0 | 7.2 | 2.4 |
| class-I MHC-restricted T cell associated molecule (CRTAM) | 36389_at | 3.3 | 11.8 | 9.4 | 12.5 |
| meningioma-expressed antigen 6 (MEA6) | 41615_at | 3.3 | 4.3 | 5.4 | 6.6 |
| hMed7 (MED7) | 36648_at | 3.3 | 3.1 | 5.1 | 6.9 |
| acetyl-coenzyme A transporter | 34668_at | 3.3 | 3.1 | 4.4 | 3.7 |
| KIAA0241 gene | 39761_at | 3.3 | 4.8 | 7.1 | 7.7 |
| gb = U00946 | 32185_at | 3.3 | 3.6 | 4.6 | 3.4 |
| gb = X53390 | 38794_at | 3.3 | 4 | 3.2 | 6.1 |
| Kruppel-type zinc finger protein | 35588_at | 3.3 | 3.3 | 6.5 | 11.8 |
| gb = AL050159 | 38717_at | 3.3 | 5.5 | 4.2 | −4.7 |
| protein-tyrosine phosphatase 1C | 794_at | 3.3 | 5.4 | 3.3 | 1.1 |
| DAP-kinase mRNA | 40049_at | 3.3 | 5.8 | 9.4 | −2.1 |
| KIAA1105 protein | 33457_at | 3.3 | 4.8 | 5.2 | 5.4 |
| son-a | 39097_at | 3.3 | 3.5 | 4 | 4.6 |
| neutral amino acid transporter B mRNA | 41778_at | 3.3 | 4.2 | 3.4 | 2.8 |
| candidate tumor suppressor gene 21 protein isoform I mRNA | 40498_g_at | 3.2 | 3 | 3.5 | 2.3 |
| KIAA0453 protein | 32743_at | 3.2 | 3.0 | 4.6 | 6.6 |
| gb = AL080133 | 41815_at | 3.2 | 4.3 | 5.5 | 4.7 |
| DMA, DMB, HLA-Z1, IPP2, LMP2, TAP1, LMP7, TAP2, DOB, DQB2 and RING8, 9, 13 and 14 genes | 41184_s_at | 3.2 | 3.5 | 3 | 2.2 |
| 2,4-dienoyl-CoA reductase gene | 38104_at | 3.2 | 4.8 | 3.4 | 3.3 |
| gb = AF055024 | 31875_at | 3.2 | 3.3 | 4.4 | 4.9 |
| KIAA0068 gene | 37306_at | 3.2 | 7.9 | 11.6 | −1.7 |
| mitochondrial 3-oxoacyl-CoA thiolase | 41530_at | 3.2 | 4.2 | 3.2 | 2.5 |
| replication protein A 70 kDa | 38481_at | 3.2 | 3.2 | 3.1 | 4.6 |
| Human Interferon-gamma induced protein (IFI 16) gene | 1456_s_at | 3.1 | 3.5 | 6 | 3.1 |
| VHL binding protein-1 (VBP-1) | 171_at | 3.1 | 3.6 | 3 | 4.5 |
| butyrophilin (BTF5) | 32629_f_at | 3.1 | 3.6 | 5.2 | 3 |
| gb = AI986201 | 35787_at | 3.1 | 4.3 | 5.1 | 7.1 |
| gb = AL050275 | 39115_at | 3.1 | 3.7 | 4.4 | 8.1 |
| gb = AI478147 | 40853_at | 3.1 | 4.1 | 4.8 | 1.7 |
| gb = AB028960 | 40829_at | 3 | 6.7 | 6.7 | 7.5 |
| gb = AL049435 | 38510_at | 3.0 | 4.5 | 9.0 | 1.2 |
| gb = AL080115 | 39442_at | 3 | 3.7 | 6.3 | 4.6 |
| Human phosphatase 2A | 924_s_at | 3 | 3.8 | 3.2 | 5 |
| WNT7a | 36763_at | 3 | 4.5 | 4.4 | 10.0 |
| skeletal muscle abundant protein | 32655_s_at | 3.0 | 3.2 | 6.0 | 7.7 |
| Gb = R59606 | 41302_at | 3 | 3.4 | 3.9 | 3.5 |

TABLE 2-continued

Genes upregulated in LGL1, LGL2 and LGL3/RA (Affymetrix U 95)

| Gene Name | Accession No. | LGL1 | LGL2 | LGL3/RA | CD8+ |
|---|---|---|---|---|---|
| | | (Fold increase compared to PBMC) | | | Normal |
| gb = AF070590 | 40760_at | 3.0 | 3.7 | 4.1 | 2.1 |
| Phosphatidylinositol-4-phosphate 5-kinase type II beta | 35741_at | 3 | 3.8 | 3.9 | 5.4 |
| KIAA0541 protein | 41430_at | 3 | 3.4 | 4.6 | 3.7 |
| FIP2 alternatively translated | 41742_s_at | 3 | 3 | 3.3 | 3.2 |

TABLE 3

Genes that are down-regulated in LGL leukemia patients when compared to normal (Affymetrix U 95)

| Name of the Gene | Accession No. | LGL 1 | LGL 2 | LGL3/RA |
|---|---|---|---|---|
| 1. KIAA0508 | 33591_at | −2.8 | −24.8 | −23.7 |
| 2. retinal short-chain dehydrogenase/reductase retSDR1 | 40782_at | −1.4 | −17.1 | −10 |
| 3. KIAA0414 | 41695_at | −2.7 | −13.1 | −8.6 |
| 4. hypothetical protein FLJ10097 | 40916_at | −1.3 | −10.5 | −6 |
| 5. KIAA0552 | 38248_at | 1.9 | −9.7 | −11.7 |
| 6. integrin alpha 6 subunit | 39753_at | −2.1 | −9.4 | −5.3 |
| 7. KIAA0172 | 37225_at | −2.2 | −9.1 | −8.6 |
| 8. two-handed zinc finger protein ZEB | 33440_at | 1.5 | −7.9 | −8.0 |
| 9. sterol-C5-desaturase | 33421_s_at | −2.4 | −7.6 | −10.0 |
| 10. nuclear factor RIP140 | 40088_at | −2.2 | −6.9 | −4.6 |
| 11. SCML2 protein | 38518_at | −2.1 | −5.8 | −5.3 |
| 12. receptor protein-tyrosine kinase (HEK8) | 1606_at | 3.5 | −5.5 | −4.8 |
| 13. hSGT1 | 33746_at | −2.9 | −5.5 | −5.4 |
| 14. gb = AL080144 | 35672_at | −2.4 | −5 | −7 |
| 15. Dr1-associated corepressor (DRAP1) | 39077_at | −1 | −4.9 | −14.7 |
| 16. collagen binding protein 2 | 39166_s_at | −2.5 | −4.7 | −7.4 |
| 17. CD44 isoform RC (CD44) | 31472_s_at | −2.3 | −4.6 | −4.6 |
| 18. USF2 | 38324_at | 2.5 | −4.5 | −5.0 |
| 19. G protein-coupled receptor (EBI 1) gene exon 3 | 1097_s_at | 3 | −4.1 | −5.4 |
| 20. serine/threonine kinase receptor-2-3 (SKR2-3) | 34055_at | −2.2 | −4.0 | −3.9 |
| 21. gb = AC002073 | 36231_at | −2.2 | −4 | −12.8 |
| 22. nel-related protein 2 | 32598_at | 4.1 | −3.9 | −5.3 |
| 23. transducin-like enhancer protein (TLE3) | 38234_at | −2.4 | −3.9 | −3.2 |
| 24. DNA binding protein (SATB1) | 36899_at | 1.5 | −3.8 | −4.7 |
| 25. KIAA0443 | 37446_at | 1.7 | −3.8 | −4.8 |
| 26. HSPNP | 430_at | −1.2 | −3.7 | −3 |
| 27. gb = AF052160 | 34962_at | −1.7 | −3.7 | −9.6 |
| 28. LIM protein SLIMMER | 32542_at | −1.1 | −3.7 | −4.8 |
| 29. calponin | 40953_at | 2.9 | −3.7 | −3.6 |
| 30. KIAA0346 | 41386_i_at | −2.2 | −3.7 | −4.1 |
| 31. nuclear factor kappa-B DNA binding subunit (NF-kappa-B) | 1378_g_at | −2.3 | −3.4 | −4.1 |
| 32. You paraneoplastic antigen (CDR2) | 36190_at | −1.2 | −3.3 | −5.8 |
| 33. cell surface glycoprotein CD44 (CD44) gene, 3 end of long tailed isoform | 1125_s_at | −2.7 | −3.1 | −3.4 |
| 34. Death Receptor 3 (DR-3, WSL-S1, Apo-3) | 41189_at | 2.3 | −3 | −3.8 |
| 35. gb = AL049365 | 34788_at | 1.2 | −3 | −7.6 |

TABLE 4

Proteolytic Enzymes upregulated (data from the analysis of Incyte Genomics)

| Gene Name | Balanced differential expression |
|---|---|
| Granzyme H | 6.3 |
| Cathepsin W (Lymphopain) | 5.4 |
| Perforin | 3.8 |
| Matrix metalloproteinase 8 | 3.2 |
| Granzyme B precursor | 3.1 |
| Calpain, small polypeptide | 2.0 |
| Granzyme A | 2.0 |
| Caspase-8 | 1.4 |

TABLE 5

Proteolytic enzymes that are upregulated in leukemic LGL (data from the analysis of Affymetrix)

| Name of the gene | Fold change compared to normal PBMC | | |
|---|---|---|---|
| | CD8+ | LGL1 | LGL2 |
| Granzyme H | 2.2 | 28.6 | 14.7 |
| Granzyme B | 1.6 | 21.8 | 10.8 |
| Perforin | 7.6 | 10.3 | 44.7 |
| Granzyme A | 1.4 | 6.6 | 5.5 |
| Cathepsin C | — | 5.6 | 5.0 |

TABLE 6

Protease inhibitors that are downregulated in leukemic LGL (data from the analysis of Affymetrix)

| Name of the gene | Fold change compared to normal PBMC | | |
|---|---|---|---|
| | CD8+ | LGL1 | LGL2 |
| Cystatin C | −97.5 | −2.9 | −1.4 |
| Cystatin A | −20.5 | −3.4 | −1.5 |
| α-1 Antitrypsin | −24.7 | −2.5 | −1.7 |
| Metalloproteinase Inhibitor | −8.5 | −4.8 | −2.4 |

TABLE 7

Lymphokine/Chemokine profile of LGL leukemia sera*

| Lymphokine/Chemokine | Elevated/Total | Average Level (pg per ml) | | Significance (P Value) |
|---|---|---|---|---|
| | | LGL | Normal | |
| RANTES | 26/27 | 17100 | 2890 | <0.001 |
| MIP-1α | 5/27 | 1151 | 1051 | =0.24 |
| MIP-1β | 16/27 | 2174 | 358 | <0.001 |
| IL-8 | 11/27 | 1097 | 405 | <0.01 |
| IL-1β | 5/27 | 596 | 784 | =0.39 |
| IL-1Ra | 9/27 | 479 | 143 | <0.02 |
| IL-18 | 16/27 | 561 | 134 | <0.005 |
| IFNγ | 11/27 | 797 | 724 | =0.26 |
| TNFα | 13/27 | 309 | 170 | =0.11 |

*Findings from cytokine ELISAs are displayed. The pg/ml of each cytokine was determined using standards of known concentrations. P values as determined from grouped findings are shown.

REFERENCES

WO 01/36646
U.S. Patent Application Publication No. 2003/0190654
U.S. Patent Application Publication No. 2003/0032594
U.S. Patent Application Publication No. 2002/0120100
U.S. Patent Application Publication No. 2002/0035243
Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.
Butz, E. A., Bevan, M. J. (1998) "Massive expansion of antigen-specific CD8+ T cells during an acute virus infection" *Immunity* 8:167-175.
Callan, M. F. C., Fazou, C., Yang, H., Rostron, T., Poon, K., Hatton, C., McMichael, A. J. (2000) "CD8+ T-cell selection, function and death in the primary immune response in vivo" *J Clin Invest* 106:1251-1261.
Crabtree, G. R., Clipstone, N. A. (1994) "Signal transmission between the plasma membrane and nucleus of T lymphocytes" *Ann Rev Biochem* 63:1045-1083.
Engler-Blum, G., Meier, M., Frank, J., Muller, G. A. (1993) "Reduction of background in problems in non-radioactive Northern blot analysis enables higher sensitivity than $^{32}$P-based hybridizations" *Anal. Biochem* 210:235-244.
Grakoui, A, Bromley, S. K., Sumen, C., Davis, M. M., Shaw, A. S., Allen, P. M., Dustin, M. L. (1999) "The immunological synapse: a molecular machine controlling T-cell activation" *Science* 285:221-227.
Hoshino, S., Oshimi, K., Teramura, M., Mizoguchi, H. (1991) "Activation via the CD3 and CD16 pathway mediates interleukin-2-dependent autocrine proliferation of granular lymphocytes in patients with granular lymphocyte proliferative disorders" *Blood* 78:3232-3240.
Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.
Karlin S. and Altschul, S. F. (1993) "Applications and Statistics for Multiple High-Scoring Segments in Molecular Sequences" *Proc. Natl. Acad. Sci. USA* 90:5873-5877.
Kasten-Sportes, C., Zaknoen, S., Steis, R. G., Chan, W. C., Winton, E. F., Waldmann, T. A. (1994) "T-cell receptor gene rearrangement in T-cell large granular leukocyte leukemia: preferential V alpha but diverse J alpha usage in one of five patients" *Blood* 83:767-775.
Kothapalli, R., Yoder, S. J., Mane, S., Loughran, T. P., Jr. (2002a) "Microarray results: how accurate are they?" *BMC Bioinformatics* 3:1-10.
Kothapalli, R., Kusmartseva, I., Loughran, M. P., Jr. (2002b) "Characterization of a human sphingosine-1-phosphate receptor gene (S1P$_5$) and its differential expression in LGL leukemia" *Biochimica et Biophysics Acta* 1579:117-123.
Kothapalli, R., Yoder, S. J., Kusmartseva, I. K., Loughran, T. P., Jr. (2003) "Characterization of a variant of PAC-1 in large granular lymphocyte leukemia" *Protein Expression & Purification* 32:52-60.
Lamy, T., Liu, J. H., Landowski, T. H., Dalton, W. S., Loughran, T. P., Jr. (1998) "Dysregulation of CD95/CD 95 ligand-apoptatic pathway in CD3+ large granular lymphocyte leukemia" *Blood* 92:4771-4777.
Lamy, T., Loughran, T. P., Jr. (1999) "Current concepts: large granular lymphocyte leukemia" *Blood Rev* 13:230-240.

Loughran, T. P., Jr., Aprile, J. A., Ruscetti, F. W. (1990) "Anti-CD3 monoclonal antibody-mediated cytotoxicity occurs through an interleukin-2-independent pathway in CD3+ large granular lymphocytes" *Blood* 75:935-940.

Loughran, T. P., Jr. (1993) "Clonal diseases of large granular lymphocytes" *Blood* 82: 1-14.

McManus, Michael T. and Phillip A. Sharp (2002) "Gene Silencing in Mammals by Small Interfering RNAs" *Nature Reviews Genetics* 3:737-747.

Maniatis, T., E. F. Fritsch, J. Sambrook (1982) "Nuclease Bal31" *Molecular Cloning: A Laboratory Manual*, Cold Spring Harbor Laboratory, Cold Spring Harbor, N.Y.

Oshimi, K., Shinkai, Y., Okumura, K., Oshimi, Y., Mizoguchi, H. (1990) "Perforin gene expression in granular lymphocyte proliferative disorders" *Blood* 75:704-708.

Nagata, S., Golstein, P. (1995) "The Fas death factor" *Science* 267:1449-1456.

Sambrook, J., Fritsch, E. F., Maniatis, T. (1989) "Plasmid Vectors" In: *Molecular Cloning. A Laboratory Manual.*, 2nd Edition., Cold Spring Harbor Laboratory Press, Cold Spring Harbor, N.Y., pp. 1-82.

Zambello, R., Trentin, L., Facco, M., Cerutti, A., Sancetta, R., Milani, A., Raimondi, R., Tassinari, C., Agostini, C., Semenzato, G. (1995) "Analysis of the T cell receptor in the lymphoproliferative disease of granular lymphocytes: superantigen activation of clonal CD3+ granular lymphocytes" *Cancer Res* 55:6140-6145.

Zimmermann, C., Rawiei, M., Blaser, C., Kaufmann, M., Pircher, H. (1996) "Homeostatic regulation of CD8+ T cells after antigen challenge in the absence of Fas (CD95)" *Eur. J. Immunol.* 26:2903-2910.

We claim:

1. A method for screening, detecting or diagnosing and treating large granular lymphocyte (LGL) leukemia in a person or animal, said method comprising obtaining a biological sample from said person or animal, and screening for or detecting upregulated expression in said biological sample of genes whose expression is upregulated in a leukemic LGL cell, wherein said genes whose expression is upregulated comprises a combination of each of granzyme A; granzyme B; granzyme H; granzyme K; cathepsin C; cathepsin W; calpain small subunit; caspase-8; perforins; A 20; phosphatase in activated cells (PAC-1); NGK2 receptors; RANTES; MIP-1alpha; MIP-1beta; IL-8; IL-1Ra; IFN-gamma; IL-18; IL-10; IL-1β; and IL-12 p35, and wherein said screening or detecting step comprises isolating RNA from a cell from said biological sample and assaying said RNA for increased levels of RNA expression of said genes as compared to levels of RNA expression of said genes from a normal cell or a non-LGL cell, wherein the level of expression of said RNA is assayed using a reverse transcription-polymerase chain reaction (RT-PCR) assay, cDNA or oligonucleotide microarray assay, or Northern blot assay; and wherein following detection or diagnosis of LGL leukemia in the person or animal, said method further comprises administering to the person or animal an anticancer compound selected from a mitotic inhibitor, an alkylating agent, an antimetabolite, a DNA intercalator, a topoisomerase inhibitor, or an antiangiogenic agent.

2. The method according to claim 1, wherein said biological sample is selected from the group consisting of bone marrow, lymph node, spleen, peripheral blood, lymph fluid, serous fluid, urine, and saliva.

3. The method according to claim 1, wherein the alkylating agent is cyclophosphamide or ifosfamide; or wherein the antimetabolite is 5-fluorouracil or hydroxyurea; or wherein the DNA intercalator is adriamycin or bleomycin; or wherein the topoisomerase inhibitor is etoposide or camptothecin; or wherein the antiangiogenic agent is angiostatin; or wherein the mitotic inhibitor is taxol or vinblastine.

4. The method according to claim 1, wherein the level of expression of said RNA is assayed using a RT-PCR assay.

5. The method according to claim 1, wherein the level of expression of said RNA is assayed using a cDNA assay.

6. The method according to claim 1, wherein the level of expression of said RNA is assayed using an oligonucleotide microarray assay.

7. The method according to claim 1, wherein the level of expression of said RNA is assayed using a Northern blot assay.

8. A method for treating a person or animal having large granular lymphocyte (LGL) leukemia, said method comprising obtaining a biological sample from said person or animal, and screening for or detecting upregulated expression in said biological sample of genes whose expression is upregulated in a leukemic LGL cell, wherein said genes whose expression is upregulated comprises a combination of each of granzyme A; granzyme B; granzyme H; granzyme K; cathepsin C; cathepsin W; calpain small subunit; caspase-8; perforins; A 20; phosphatase in activated cells (PAC-1); NGK2 receptors; RANTES; MIP-1alpha; MIP-1beta; IL-8; IL-1Ra; IFN-gamma; IL-18; IL-10; IL-1β; and IL-12 p35, and wherein said screening or detecting step comprises isolating RNA from a cell from said biological sample and assaying said RNA for increased levels of RNA expression of said genes as compared to levels of RNA expression of said genes from a normal cell or a non-LGL cell, wherein the level of expression of said RNA is assayed using a reverse transcription-polymerase chain reaction (RT-PCR) assay, cDNA or oligonucleotide microarray assay, or Northern blot assay; and wherein following detection or diagnosis of LGL leukemia in the person or animal, said method further comprises administering to the person or animal an anticancer compound selected from a mitotic inhibitor, an alkylating agent, an antimetabolite, a DNA intercalator, a topoisomerase inhibitor, or an antiangiogenic agent.

9. The method according to claim 8, wherein the alkylating agent is cyclophosphamide or ifosfamide; or wherein the antimetabolite is 5-fluorouracil or hydroxyurea; or wherein the DNA intercalator is adriamycin or bleomycin; or wherein the topoisomerase inhibitor is etoposide or camptothecin; or wherein the antiangiogenic agent is angiostatin; or wherein the mitotic inhibitor is taxol or vinblastine.

10. The method according to claim 8, wherein the level of expression of said RNA is assayed using a RT-PCR assay.

11. The method according to claim 8, wherein the level of expression of said RNA is assayed using a cDNA assay or an oligonucleotide microarray assay.

12. The method according to claim 8, wherein the level of expression of said RNA is assayed using a Northern blot assay.

* * * * *

UNITED STATES PATENT AND TRADEMARK OFFICE
CERTIFICATE OF CORRECTION

PATENT NO. : 9,513,286 B2
APPLICATION NO. : 11/476407
DATED : December 6, 2016
INVENTOR(S) : Thomas P. Loughran and Ravi Kothapalli It is certified that error appears in the above-identified patent and that said Letters Patent is hereby corrected as shown below:

Column 27,
Line 5, "PBMC) Normal" should read --Normal PBMC)--.

Column 29,
Line 5, "PBMC) Normal" should read --Normal PBMC)--.

Column 31,
Line 5, "PBMC) Normal" should read --Normal PBMC)--.

Column 33,
Line 5, "PBMC) Normal" should read --Normal PBMC)--.

Column 35,
Line 5, "PBMC) Normal" should read --Normal PBMC)--.

Column 37,
Line 5, "PBMC) Normal" should read --Normal PBMC)--.

Column 39,
Line 5, "PBMC) Normal" should read --Normal PBMC)--.

Column 41,
Line 5, "PBMC) Normal" should read --Normal PBMC)--.

Column 43,
Line 5, "PBMC) Normal" should read --Normal PBMC)--.

Column 45,
Line 5, "PBMC) Normal" should read --Normal PBMC)--.

Signed and Sealed this
Eleventh Day of September, 2018

Andrei Iancu
*Director of the United States Patent and Trademark Office*